US006372488B1

(12) United States Patent
Kamboj et al.

(10) Patent No.: US 6,372,488 B1
(45) Date of Patent: Apr. 16, 2002

(54) AMPA-BINDING HUMAN GLUR4 RECEPTORS

(75) Inventors: Rajender Kamboj, Mississauga; Candace E. Elliott; Stephen L. Nutt, both of Etobicoke, all of (CA)

(73) Assignee: NPS Allelix Corp., Mississauga (CA)

( * ) Notice: Subject to any disclaimer, the term of this patent is extended or adjusted under 35 U.S.C. 154(b) by 0 days.

(21) Appl. No.: 08/473,204

(22) Filed: Jun. 7, 1995

Related U.S. Application Data

(62) Division of application No. 08/259,164, filed on Jun. 13, 1994, now Pat. No. 5,643,785, which is a continuation of application No. 07/924,553, filed on Aug. 5, 1992, now abandoned.

(51) Int. Cl.[7] .......................... C12N 5/10; C12N 15/12; C07K 14/705
(52) U.S. Cl. ............... 435/325; 435/252.3; 435/254.11; 435/69.1; 530/350; 536/23.5
(58) Field of Search .............................. 435/69.1, 252.3, 435/320.1, 41, 254.11; 536/23.5; 530/350

(56) References Cited

FOREIGN PATENT DOCUMENTS

| WO | WO 91/06648 | 5/1991 |
|---|---|---|
| WO | WO 92/10583 | 6/1992 |

OTHER PUBLICATIONS

Cutting et al, *P.N.A.S.* 88: 2673:2677, Apr. 1991.*
Grandy et al, *P.N.A.S.* 86: 9762–9766, Dec. 1989.*
Hollmann et al. (1989) *Nature* 342: 643–646 "Cloning by functional expression of a member of the glutamate receptor family".
Keinanen et al. (1990) *Science* 249: 556–560 "A family of AMPA-selective glutamate receptors".
Boulter et al. (1990) *Science* 249: 1033–1037 "Molecular cloning and functional expression of glutamate receptor subunit genes".
Bettler et al. (1990) *Neuron* 5: 583–595 "Cloning of a novel glutamate receptor unit, GluR5: expression in the nervous system during development".
Sommer et al. (1990) *Science* 249: 1580–1585 "Flip and flop: a cell-specific functional switch in glutamate-operated channels of the CNS".
Monyer et al. (1991) *Neuron* 6: 799–810 "Glutamate-operated channels: developmentally early and mature forms arise by alternative splicing".
Nakanashi et al. (1990) *Neuron* 5: 569–581 "A family of glutamate receptor genes: evidence for the formation of heteromultimeric receptors with distinct channel receptors".
Hollmann et al. (1991) *Science* 252: 851–853 "$Ca^{2+}$ permeability of KA–AMPA–gated glutamate receptor channels depends on subunit composition".
Verdoorn et al. (1991) *Science* 252: 1715–1718 "Structural determinants of ion flow through recombinant glutamate receptor channels".
Egebjerg et al. (1991) *Nature* 351: 745–748 "Cloning of a cDNA for a glutamate receptor subunit activated by kainate but not AMPA".
Wada et al. (1991) *Nature* 342: 684–689 "Sequence and expression of a frog brain complementary DNA encoding a kainate–binding protein".
Gregor et al. (1989) *Nature* 342: 689–692 "Molecular structure of the chick cerebellar kainate–binding subunit of a putative glutamate receptor".
Werner et al. (1991) *Nature* 351: 742–744 "Cloning of a putative high–affinity kainate receptor expressed predominantly in hippocampal CA3 cells".
Verdoorn et al. (1988) *Mol. Pharmacol.* 34: 298–307 "Excitatory amino acid receptors expressed in *Xenopus oocytes*: agonist pharmacology".
William Sun, et al., "Molecular cloning, chromosomal mapping, and functional expression of human brain . . . "; Proc. Natl. Acad. Sci. USA, vol. 89, pp. 1443–1447, Feb. 1992.
Carmie Puckett, et al., "Molecular cloning and chromosomal localization of one of the human . . . "; Proc. Natl. Acad. Sci. USA, vol. 88, pp. 7557–7561, Sep. 1991.
McNamara et al., Chromosomal Localization of Human Glutamate Receptor Genes, Journal of Neuroscience, Jul. 1992, 12(7): 2555–2562.
Jansen et al., Neuroscience (1989) 32:587–607.

* cited by examiner

*Primary Examiner*—Lorraine Spector
*Assistant Examiner*—Claire M. Kaufman
(74) *Attorney, Agent, or Firm*—Foley & Lardner

(57) ABSTRACT

Described herein are isolated polynucleotides which code for an AMPA-type human CNS receptor, designated the human GluR4B receptor. The receptor is characterized structurally and the construction and use of cell lines expressing the receptor is disclosed.

1 Claim, 10 Drawing Sheets

FIG. 1A

```
       EcoRI
       |
       GAATTCCGAGAGAGAGCGCGCGCCAGGGAGAGGAGAAAAGAAGATGAGGATTATTTCCAG
   1   ---------+---------+---------+---------+---------+---------+ 60
       CTTAAGGCTCTCTCTCGCGCGCGGTCCCTCTCCTCTTTTCTTCTACTCCTAATAAAGGTC
                                                   M  R  I  I  S  R

ACAGATTGTCTTGTTATTTTCTGGATTTTGGGGACTCGCCATGGGAGCCTTTCCGAGCAG
  61   ---------+---------+---------+---------+---------+---------+ 120
       TGTCTAACAGAACAATAAAAGACCTAAAACCCCTGAGCGGTACCCTCGGAAAGGCTCGTC
        Q  I  V  L  L  F  S  G  F  W  G  L  A  M  G  A  F  P  S  S   5
                                                       |_MatureN-Terminus CGTGCAAATAGGTGGTCTCTTCATCCGAAACACAGATCAGGAATACACTGCTTTTCGATT
 121   ---------+---------+---------+---------+---------+---------+ 180
       GCACGTTTATCCACCAGAGAAGTAGGCTTTGTGTCTAGTCCTTATGTGACGAAAAGCTAA
          V  Q  I  G  G  L  F  I  R  N  T  D  Q  E  Y  T  A  F  R  L AGCAATTTTTCTTCATAACACCGCCCCCAATGCGTCGGAAGCTCCTTTTAATTTGGTACC
 181   ---------+---------+---------+---------+---------+---------+ 240
       TCGTTAAAAAGAAGTATTGTGGCGGGGGTTACGCAGCCTTCGAGGAAAATTAAACCATGG
          A  I  F  L  H  N  T  A  P  N  A  S  E  A  P  F  N  L  V  P TCATGTGGACAACATTGAGACAGCCAACAGTTTTGCTGTAACAAACGCCTTCTGTTCCCA
 241   ---------+---------+---------+---------+---------+---------+ 300
       AGTACACCTGTTGTAACTCTGTCGGTTGTCAAAACGACATTGTTTGCGGAAGACAAGGGT
          H  V  D  N  I  E  T  A  N  S  F  A  V  T  N  A  F  C  S  Q GTATTCTAGAGGAGTATTTGCCATTTTTGGACTCTATGATAAGAGGTCGGTACATACCTT
 301   ---------+---------+---------+---------+---------+---------+ 360
       CATAAGATCTCCTCATAAACGGTAAAAACCTGAGATACTATTCTCCAGCCATGTATGGAA
          Y  S  R  G  V  F  A  I  F  G  L  Y  D  K  R  S  V  H  T  L PstI
              |
       GACCTCATTCTGCAGCGCCTTACATATCTCCCTCATCACACCAAGTTTCCCTACTGAGGG
 361   ---------+---------+---------+---------+---------+---------+ 420
       CTGGAGTAAGACGTCGCGGAATGTATAGAGGGAGTAGTGTGGTTCAAAGGGATGACTCCC
          T  S  F  C  S  A  L  H  I  S  L  I  T  P  S  F  P  T  E  G 105

GGAGAGCCAGTTTGTGCTGCAACTAAGACCTTCGTTACGAGGAGCACTCTTGAGTTTGCT
 421   ---------+---------+---------+---------+---------+---------+ 480
       CCTCTCGGTCAAACACGACGTTGATTCTGGAAGCAATGCTCCTCGTGAGAACTCAAACGA
          E  S  Q  F  V  L  Q  L  R  P  S  L  R  G  A  L  L  S  L  L

GGATCACTACGAATGGAACTGTTTTGTCTTCCTGTATGACACAGACAGGGGATACTCGAT
 481   ---------+---------+---------+---------+---------+---------+ 540
       CCTAGTGATGCTTACCTTGACAAAACAGAAGGACATACTGTGTCTGTCCCCTATGAGCTA
          D  H  Y  E  W  N  C  F  V  F  L  Y  D  T  D  R  G  Y  S  I
```

FIG. 1B

```
     ACTCCAAGCTATTATGGAAAAAGCAGGACAAAATGGTTGGCATGTCAGCGCTATATGTGT
541  ---------+---------+---------+---------+---------+---------+ 600
     TGAGGTTCGATAATACCTTTTTCGTCCTGTTTTACCAACCGTACAGTCGCGATATACACA
      L  Q  A  I  M  E  K  A  G  Q  N  G  W  H  V  S  A  I  C  V

GGAAAATTTTAATGATGTCAGCTATAGGCAACTTCTAGAAGAACTTGACAGAAGACAAGA
601  ---------+---------+---------+---------+---------+---------+ 660
     CCTTTTAAAATTACTACAGTCGATATCCGTTGAAGATCTTCTTGAACTGTCTTCTGTTCT
      E  N  F  N  D  V  S  Y  R  Q  L  L  E  E  L  D  R  R  Q  E

GAAGAAGTTTGTAATAGACTGTGAGATAGAGAGACTTCAAAACATATTAGAACAGATTGT
661  ---------+---------+---------+---------+---------+---------+ 720
     CTTCTTCAAACATTATCTGACACTCTATCTCTCTGAAGTTTTGTATAATCTTGTCTAACA
      K  K  F  V  I  D  C  E  I  E  R  L  Q  N  I  L  E  Q  I  V  205

AAGTGTTGGAAAGCATGTTAAAGGCTACCATTATATCATTGCAAACTTGGGATTCAAGGA
721  ---------+---------+---------+---------+---------+---------+ 780
     TTCACAACCTTTCGTACAATTTCCGATGGTAATATAGTAACGTTTGAACCCTAAGTTCCT
      S  V  G  K  H  V  K  G  Y  H  Y  I  I  A  N  L  G  F  K  D

TATTTCTCTTGAGAGGTTTATACATGGTGGAGCCAATGTTACTGGATTCCAGTTGGTGGA
781  ---------+---------+---------+---------+---------+---------+ 840
     ATAAAGAGAACTCTCCAAATATGTACCACCTCGGTTACAATGACCTAAGGTCAACCACCT
      I  S  L  E  R  F  I  H  G  G  A  N  V  T  G  F  Q  L  V  D

TTTTAATACACCCATGGTAACCAAACTAATGGATCGCTGGAAGAAACTAGATCAGAGAGA
841  ---------+---------+---------+---------+---------+---------+ 900
     AAAATTATGTGGGTACCATTGGTTTGATTACCTAGCGACCTTCTTTGATCTAGTCTCTCT
      F  N  T  P  M  V  T  K  L  M  D  R  W  K  K  L  D  Q  R  E

GTATCCAGGATCTGAGACTCCTCCAAAGTACACCTCTGCTCTGACTTATGATGGAGTCCT
901  ---------+---------+---------+---------+---------+---------+ 960
     CATAGGTCCTAGACTCTGAGGAGGTTTCATGTGGAGACGAGACTGAATACTACCTCAGGA
      Y  P  G  S  E  T  P  P  K  Y  T  S  A  L  T  Y  D  G  V  L

TGTGATGGCTGAAACTTTCCGAAGTCTTAGGAGGCAGAAAATTGATATCTCAAGGAGAGG
961  ---------+---------+---------+---------+---------+---------+ 1020
     ACACTACCGACTTTGAAAGGCTTCAGAATCCTCCGTCTTTTAACTATAGAGTTCCTCTCC
      V  M  A  E  T  F  R  S  L  R  R  Q  K  I  D  I  S  R  R  G  305

AAAGTCTGGGGATTGTCTGGCAAATCCTGCTGCTCCATGGGGCCAGGGAATTGACATGGA
1021 ---------+---------+---------+---------+---------+---------+ 1080
     TTTCAGACCCCTAACAGACCGTTTAGGACGACGAGGTACCCCGGTCCCTTAACTGTACCT
      K  S  G  D  C  L  A  N  P  A  A  P  W  G  Q  G  I  D  M  E
                              EcoRI
                              |
     GAGGACACTCAAACAGGTTCGAATTCAAGGGCTGACAGGGAATGTTCAGTTTGACCACTA
1081 ---------+---------+---------+---------+---------+---------+ 1140
     CTCCTGTGAGTTTGTCCAAGCTTAAGTTCCCGACTGTCCCTTACAAGTCAAACTGGTGAT
      R  T  L  K  Q  V  R  I  Q  G  L  T  G  N  V  Q  F  D  H  Y
```

FIG. 1C

```
     TGGACGTAGAGTCAATTACACAATGGATGTGTTTGAGCTGAAAAGCACAGGACCTAGAAA
1141 ------------------------------------------------------------+1200
     ACCTGCATCTCAGTTAATGTGTTACCTACACAAACTCGACTTTTCGTGTCCTGGATCTTT
      G  R  R  V  N  Y  T  M  D  V  F  E  L  K  S  T  G  P  R  K

GGTTGGTTACTGGAATGATATGGATAAGTTAGTCTTGATTCAAGATGTACCAACTCTTGG
1201 ------------------------------------------------------------+1260
     CCAACCAATGACCTTACTATACCTATTCAATCAGAACTAAGTTCTACATGGTTGAGAACC
      V  G  Y  W  N  D  M  D  K  L  V  L  I  Q  D  V  P  T  L  G

CAATGACACAGCTGCTATTGAGAACAGAACAGTGGTTGTAACCACAATTATGGAATCCCC
1261 ------------------------------------------------------------+1320
     GTTACTGTGTCGACGATAACTCTTGTCTTGTCACCAACATTGGTGTTAATACCTTAGGGG
      N  D  T  A  A  I  E  N  R  T  V  V  V  T  T  I  M  E  S  P  405

ATATGTTATGTACAAGAAAAATCATGAAATGTTTGAAGGAAATGACAAGTATGAAGGATA
1321 ------------------------------------------------------------+1380
     TATACAATACATGTTCTTTTTAGTACTTTACAAACTTCCTTTACTGTTCATACTTCCTAT
      Y  V  M  Y  K  K  N  H  E  M  F  E  G  N  D  K  Y  E  G  Y

CTGTGTAGATTTGGCATCTGAAATTGCAAAACATATTGGTATCAAGTATAAAATTGCCAT
1381 ------------------------------------------------------------+1440
     GACACATCTAAACCGTAGACTTTAACGTTTTGTATAACCATAGTTCATATTTTAACGGTA
      C  V  D  L  A  S  E  I  A  K  H  I  G  I  K  Y  K  I  A  I

TGTCCCTGATGGAAAATATGGAGCAAGGGATGCAGACACAAAAATCTGGAATGGGATGGT
1441 ------------------------------------------------------------+1500
     ACAGGGACTACCTTTTATACCTCGTTCCCTACGTCTGTGTTTTAGACCTTACCCTACCA
      V  P  D  G  K  Y  G  A  R  D  A  D  T  K  I  W  N  G  M  V

AGGAGAACTTGTTTATGGGAAAGCAGAGATTGCTATTGCCCCTCTGACAATCACTTTGGT
1501 ------------------------------------------------------------+1560
     TCCTCTTGAACAAATACCCTTTCGTCTCTAACGATAACGGGGAGACTGTTAGTGAAACCA
      G  E  L  V  Y  G  K  A  E  I  A  I  A  P  L  T  I  T  L  V

ACGAGAGGAGGTCATTGACTTTTCTAAGCCCTTCATGAGTTTGGGCATATCTATCATGAT
1561 ------------------------------------------------------------+1620
     TGCTCTCCTCCAGTAACTGAAAAGATTCGGGAAGTACTCAAACCCGTATAGATAGTACTA
      R  E  E  V  I  D  F  S  K  P  F  M  S  L  G  I  S  I  M  I  505

CAAAAAGCCTCAGAAATCCAAACCAGGAGTGTTTTCCTTCTTGGATCCTCTGGCCTATGA
1621 ------------------------------------------------------------+1680
     GTTTTTCGGAGTCTTTAGGTTTGGTCCTCACAAAAGGAAGAACCTAGGAGACCGGATACT
      K  K  P  Q  K  S  K  P  G  V  F  S  F  L  D  P  L  A  Y  E

GATTTGGATGTGCATAGTCTTTGCCTACATTGGTGTCAGCGTGGTCTTATTCCTAGTTAG
1681 ------------------------------------------------------------+1740
     CTAAACCTACACGTATCAGAAACGGATGTAACCACAGTCGCACCAGAATAAGGATCAATC
      I  W  M  C  I  V  F  A  Y  I  G  V  S  V  V  L  F  L  V  S
```

FIG. 1D

```
         TAGATTTAGTCCATATGAGTGGCACACAGAAGAGCCAGAGGACGGAAAGGAAGGACCCAG
1741     ---------+---------+---------+---------+---------+---------+ 1800
         ATCTAAATCAGGTATACTCACCGTGTGTCTTCTCGGTCTCCTGCCTTTCCTTCCTGGGTC
          R  F  S  P  Y  E  W  H  T  E  E  P  E  D  G  K  E  G  P  S

CGACCAGCCTCCCAATGAGTTTGGCATCTTTAACAGCCTCTGGTTTTCCCTGGGTGCTTT
1801     ---------+---------+---------+---------+---------+---------+ 1860
         GCTGGTCGGAGGGTTACTCAAACCGTAGAAATTGTCGGAGACCAAAAGGGACCCACGAAA
          D  Q  P  P  N  E  F  G  I  F  N  S  L  W  F  S  L  G  A  F

TATGCAGCAAGGATGTGACATTTCACCCAGATCCCTCTCAGGTCGAATTGTTGGAGGTGT
1861     ---------+---------+---------+---------+---------+---------+ 1920
         ATACGTCGTTCCTACACTGTAAAGTGGGTCTAGGGAGAGTCCAGCTTAACAACCTCCACA
          M  Q  Q  G  C  D  I  S  P  R  S  L  S  G  R  I  V  G  V   605

TTGGTGGTTCTTTACACTCATCATTATATCATCTTATACTGCTAACCTGGCTGCTTTCCT
1921     ---------+---------+---------+---------+---------+---------+ 1980
         AACCACCAAGAAATGTGAGTAGTAATATAGTAGAATATGACGATTGGACCGACGAAAGGA
          W  W  F  F  T  L  I  I  I  S  S  Y  T  A  N  L  A  A  F  L

GACGGTTGAGCGAATGGTCTCTCCCATAGAAAGTGCAGAAGACCTGGCCAAACAAACAGA
1981     ---------+---------+---------+---------+---------+---------+ 2040
         CTGCCAACTCGCTTACCAGAGAGGGTATCTTTCACGTCTTCTGGACCGGTTTGTTTGTCT
          T  V  E  R  M  V  S  P  I  E  S  A  E  D  L  A  K  Q  T  E
                                                       EcoRI
                                                         |
         AATTGCCTATGGAACACTGGATTCAGGATCAACAAAAGAATTCTTCAGAAGATCAAAAAT
2041     ---------+---------+---------+---------+---------+---------+ 2100
         TTAACGGATACCTTGTGACCTAAGTCCTAGTTGTTTTCTTAAGAAGTCTTCTAGTTTTTA
          I  A  Y  G  T  L  D  S  G  S  T  K  E  F  F  R  R  S  K  I

AGCAGTGTATGAAAAGATGTGGACCTACATGCGATCAGCAGAGCCATCAGTATTCACTAG
2101     ---------+---------+---------+---------+---------+---------+ 2160
         TCGTCACATACTTTTCTACACCTGGATGTACGCTAGTCGTCTCGGTAGTCATAAGTGATC
          A  V  Y  E  K  M  W  T  Y  M  R  S  A  E  P  S  V  F  T  R

GACTACAGCTGAGGGAGTAGCTCGTGTCCGCAAATCCAAGGGCAAATTTGCCTTTCTCCT
2161     ---------+---------+---------+---------+---------+---------+ 2220
         CTGATGTCGACTCCCTCATCGAGCACAGGCGTTTAGGTTCCCGTTTAAACGGAAAGAGGA
          T  T  A  E  G  V  A  R  V  R  K  S  K  G  K  F  A  F  L  L   705

GGAGTCCACTATGAATGATAACATTGAGCAGCGAAAGCCATGTGACACGATGAAAGTGGG
2221     ---------+---------+---------+---------+---------+---------+ 2280
         CCTCAGGTGATACTTACTATTGTAACTCGTCGCTTTCGGTACACTGTGCTACTTTCACCC
          E  S  T  M  N  D  N  I  E  Q  R  K  P  C  D  T  M  K  V  G

AGGAAATCTGGATTCCAAAGGCTATGGAGTAGCAACGCCCAAGGGTTCCTCATTAAGAAC
2281     ---------+---------+---------+---------+---------+---------+ 2340
         TCCTTTAGACCTAAGGTTTCCGATACCTCATCGTTGCGGGTTCCCAAGGAGTAATTCTTG
          G  N  L  D  S  K  G  Y  G  V  A  T  P  K  G  S  S  L  R  T
```

FIG. 1E

```
           TCCTGTAAACCTTGCCGTTTTGAAACTCAGTGAGGCAGGCGTCTTAGACAAGCTGAAAAA
2341       ---------+---------+---------+---------+---------+---------+ 2400
           AGGACATTTGGAACGGCAAAACTTTGAGTCACTCCGTCCGCAGAATCTGTTCGACTTTTT
            P  V  N  L  A  V  L  K  L  S  E  A  G  V  L  D  K  L  K  N

CAAATGGTGGTACGATAAAGGTGAATGTGGACCCAAAGACTCTGGAAGCAAGGACAAGAC
2401       ---------+---------+---------+---------+---------+---------+ 2460
           GTTTACCACCATGCTATTTCCACTTACACCTGGGTTTCTGAGACCTTCGTTCCTGTTCTG
            K  W  W  Y  D  K  G  E  C  G  P  K  D  S  G  S  K  D  K  T

GAGTGCCTTGAGCCTGAGCAATGTAGCAGGCGTCTTCTACATTCTGGTTGGCGGCTTGGG
2461       ---------+---------+---------+---------+---------+---------+ 2520
           CTCACGGAACTCGGACTCGTTACATCGTCCGCAGAAGATGTAAGACCAACCGCCGAACCC
            S  A  L  S  L  S  N  V  A  G  V  F  Y  I  L  V  G  G  L  G  805

CTTGGCAATGCTGGTGGCTTTGATAGAGTtCTGTTACAAGTCCAGGGCAGAAGCGAAGAG
2521       ---------+---------+---------+---------+---------+---------+ 2580
           GAACCGTTACGACCACCGAAACTATCTCAaGACAATGTTCAGGTCCCGTCTTCGCTTCTC
            L  A  M  L  V  A  L  I  E  F  C  Y  K  S  R  A  E  A  K  R

AATGAAGCTGACCTTTTCTGAAGCCATAAGAAACAAAGCCAGATTATCCATCACTGGGAG
2581       ---------+---------+---------+---------+---------+---------+ 2640
           TTACTTCGACTGGAAAAGACTTCGGTATTCTTTGTTTCGGTCTAATAGGTAGTGACCCTC
            M  K  L  T  F  S  E  A  I  R  N  K  A  R  L  S  I  T  G  S

TGTGGGAGAGAATGGCCGCGTCTTGACGCCTGACTGCCCAAAGGCTGTACACACTGGAAC
2641       ---------+---------+---------+---------+---------+---------+ 2700
           ACACCCTCTCTTACCGGCGCAGAACTGCGGACTGACGGGTTTCCGACATGTGTGACCTTG
            V  G  E  N  G  R  V  L  T  P  D  C  P  K  A  V  H  T  G  T

TGCAATCAGACAAAGTTCAGGATTGGCTGTCATTGCATCGGACCTACCATAAAAACCAAA
2701       ---------+---------+---------+---------+---------+---------+ 2760
           ACGTTAGTCTGTTTCAAGTCCTAACCGACAGTAACGTAGCCTGGATGGTATTTTGGTTT
            A  I  R  Q  S  S  G  L  A  V  I  A  S  D  L  P  *           881

AAAATAATTGAGTGCCTTAATTAAACTGTTGGTGACTGGTGGAAACGCAGCCCTGAGGGA
2761       ---------+---------+---------+---------+---------+---------+ 2820
           TTTTATTAACTCACGGAATTAATTTGACAACCACTGACCACCTTTGCGTCGGGACTCCCT

CAGCCACGCGCGGGTCTTTGCTAAACCAATCCTTTGGCTGAGAGCGGGAAGTCCGTCCTA
2821       ---------+---------+---------+---------+---------+---------+ 2880
           GTCGGTGCGCGCCCAGAAACGATTTGGTTAGGAAACCGACTCTCGCCCTTCAGGCAGGAT

Ecl136II
                                                                 |
           ACGCGCTGGCCGGACATCAGCAGCAGCAACGTGTGCATGAGCTCAGCTCGGAAACCCAAA
2881       ---------+---------+---------+---------+---------+---------+ 2940
           TGCGCGACCGGCCTGTAGTCGTCGTCGTTGCACACGTACTCGAGTCGAGCCTTTGGGTTT

CTCAGATTTTATATCAGGAAAACTCACAATTGAGGTTTTTTTCGGGGAGTGGGTGGGGA
2941       ---------+---------+---------+---------+---------+---------+ 3000
           GAGTCTAAAATATAGTCCTTTTGAGTGTTAACTCCAAAAAAAGCCCCTCACCCACCCCCT
```

FIG. 1F

```
         GGGATCTGGGATGGGTGTATTAACAGCAACAAATTTCATTCGAGTGGACTCAAAAACTAA
3001     ---------+---------+---------+---------+---------+---------+ 3060
         CCCTAGACCCTACCCACATAATTGTCGTTGTTTAAAGTAAGCTCACCTGAGTTTTTGATT

TCAGACTTATGAGTTAGCGCATTAAACTGTGAAGTTCTTGCTCAGAAAGGCCTTTGTCTT
3061     ---------+---------+---------+---------+---------+---------+ 3120
         AGTCTGAATACTCAATCGCGTAATTTGACACTTCAAGAACGAGTCTTTCCGGAAACAGAA

CACCGGAAAGGATAAAATAGTTGTAGAAGTCCGTGAACATGCTAACCTGTGTCTCCAGAA
3121     ---------+---------+---------+---------+---------+---------+ 3180
         GTGGCCTTTCCTATTTTATCAACATCTTCAGGCACTTGTACGATTGGACACAGAGGTCTT

CATCCATATAGTCCATGGAAGAAAATCCAGCTGAGAAAACAAATCACTAAACTGTGATAA
3181     ---------+---------+---------+---------+---------+---------+ 3240
         GTAGGTATATCAGGTACCTTCTTTTAGGTCGACTCTTTTGTTTAGTGATTTGACACTATT

GAAAATAATGAACAAACATGTAAAACCTGTGGGAAAAAAAAAATAAAGGAAGTATGTACA
3241     ---------+---------+---------+---------+---------+---------+ 3300
         CTTTTATTACTTGTTTGTACATTTTGGACACCCTTTTTTTTTATTTCCTTCATACATGT

CTTACTTTGGAGAAAACAAATACTGAAACATGCTTGCTTTTTAACTGACGTAAATTCAGT
3301     ---------+---------+---------+---------+---------+---------+ 3360
         GAATGAAACCTCTTTTGTTTATGACTTTGTACGAACGAAAAATTGACTGCATTTAAGTCA

AGAGGACAACACAATTCTTTTTTCTAACCATCTTAGGGAACAATACATTGCAATAATTGA
3361     ---------+---------+---------+---------+---------+---------+ 3420
         TCTCCTGTTGTGTTAAGAAAAAGATTGGTAGAATCCCTTGTTATGTAACGTTATTAACT

TATAAATGCCATCACTGTAATAAACTTTAGAGACTTTTTTTATAAAAGTTGTTGGTCAT
3421     ---------+---------+---------+---------+---------+---------+ 3480
         ATATTTACGGTAGTGACATTATTTGAAATCTCTGAAAAAAAATATTTTCAACAACCAGTA

CTTCTTGTTTGCTGTAACCTTCACTATGTCACATGAGTCGATTCACCGATTGCATTTGTC
3481     ---------+---------+---------+---------+---------+---------+ 3540
         GAAGAACAAACGACATTGGAAGTGATACAGTGTACTCAGCTAAGTGGCTAACGTAAACAG

TCACAACCAGGAAGAAAAGCAAAAGGAAGAAAACGTTTAGGTTCAATCATCAGTCTGCGG
3541     ---------+---------+---------+---------+---------+---------+ 3600
         AGTGTTGGTCCTTCTTTTCGTTTTCCTTCTTTTGCAAATCCAAGTTAGTAGTCAGACGCC

TGTAGACTCGAAAGAGATGACAGGTCACTCATGTTAATGGTATTATTTATAATCTCATTC
3601     ---------+---------+---------+---------+---------+---------+ 3660
         ACATCTGAGCTTTCTCTACTGTCCAGTGAGTACAATTACCATAATAAATATTAGAGTAAG

TGTGTACAACATTGTGGTTTTTGTACCCACCAAAAAGAATAAAACAGCAGATGTTCTTAC
3661     ---------+---------+---------+---------+---------+---------+ 3720
         ACACATGTTGTAACACCAAAAACATGGGTGGTTTTCTTATTTGTCGTCTACAAGAATG

AATATCTACAGAGCTTAAAAGTTTTTTCTTATCGTTATAAAAGTTATTTGAGAAATTATA
3721     ---------+---------+---------+---------+---------+---------+ 3780
         TTATAGATGTCTCGAATTTTCAAAAAAGAATAGCAATATTTTCAATAAACTCTTTAATAT
```

FIG. 1G

```
         AGACTATAAGAGAGATTGTATTAGTGGTGGGCCATAGTGGAAAATGTAGCTAGCCCTCAT
3781  ----------+---------+---------+---------+---------+---------+ 3840
         TCTGATATTCTCTCTAACATAATCACCACCCGGTATCACCTTTTACATCGATCGGGAGTA

TATTTTTTGCATACTAAGCTACCCCTCCTTTTCAGATCTTTGACTCATTAACAGATTAAA
3841  ----------+---------+---------+---------+---------+---------+ 3900
         ATAAAAAACGTATGATTCGATGGGGAGGAAAAGTCTAGAAACTGAGTAATTGTCTAATTT

EcoRI
                                                        |
         CTGTCAAAGATGGAGTCTTTGAGTTGGGGAATGAATCACTGTCGGAATTCCATCTTTGGA
3901  ----------+---------+---------+---------+---------+---------+ 3960
         GACAGTTTCTACCTCAGAAACTCAACCCCTTACTTAGTGACAGCCTTAAGGTAGAAACCT

HindIII
                           |
         CACCTGAAGAAAATCAAGCTT
3961  ----------+---------+-  3981
         GTGGACTTCTTTTAGTTCGAA
```

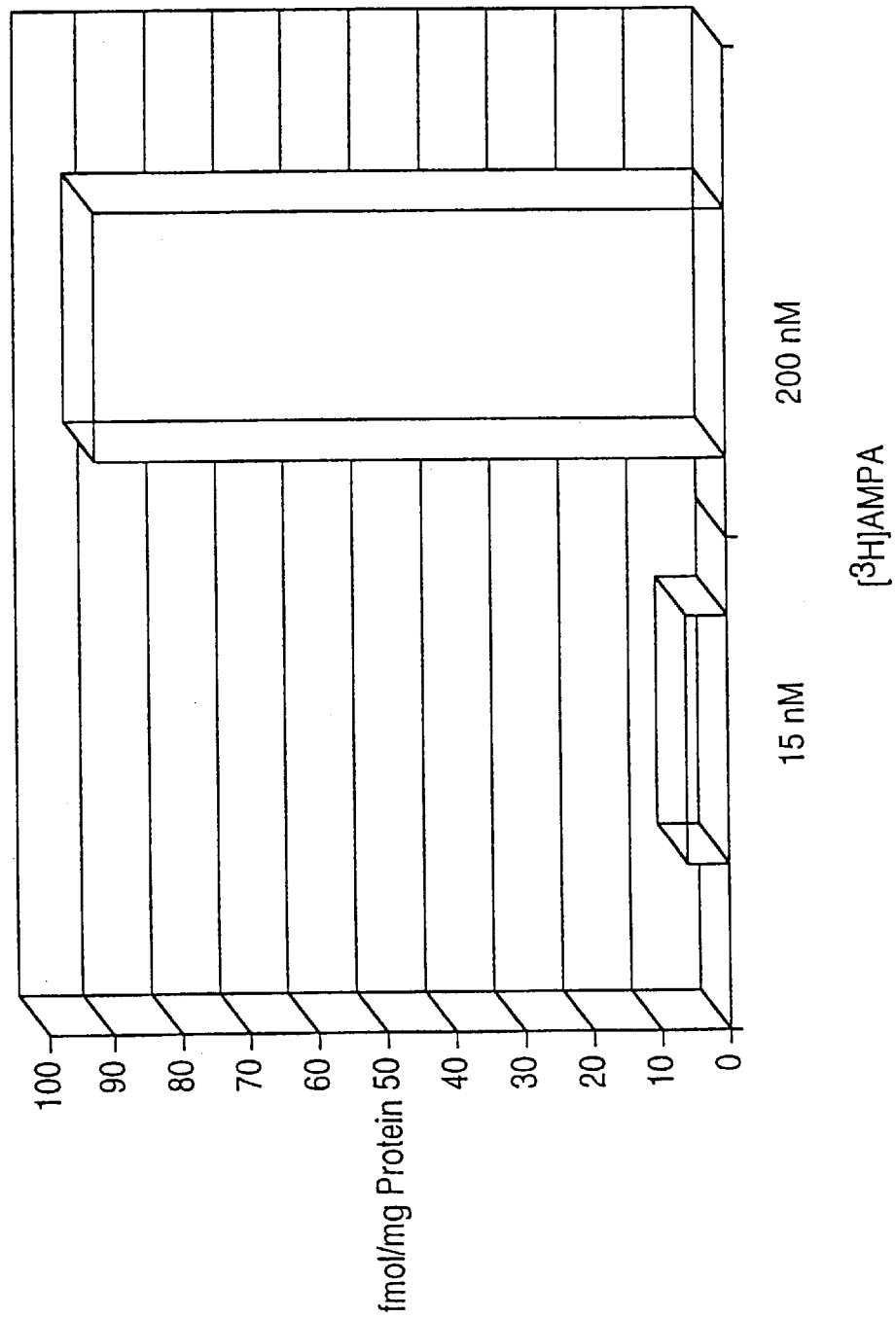

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 3981 base pairs
      (B) TYPE: nucleic acid
      (C) STRANDEDNESS: double
      (D) TOPOLOGY: linear (ix) FEATURE:
      (A) NAME/KEY: sig_peptide
      (B) LOCATION: 44..106

(ix) FEATURE:
      (A) NAME/KEY: mat_peptide
      (B) LOCATION: 107..2752

(ix) FEATURE:
      (A) NAME/KEY: CDS
      (B) LOCATION: 44..2752

(xi) SEQUENCE DESCRIPTION: SEQ ID NO:1:

```
GAATTCCGAG AGAGAGCGCG CGCCAGGGAG AGGAGAAAAG AAG ATG AGG ATT ATT      55
                                             Met Arg Ile Ile
                                             -21 -20

TCC AGA CAG ATT GTC TTG TTA TTT TCT GGA TTT TGG GGA CTC GCC ATG     103
Ser Arg Gln Ile Val Leu Leu Phe Ser Gly Phe Trp Gly Leu Ala Met
    -15                 -10                 -5
```

-continued

```
GGA GCC TTT CCG AGC AGC GTG CAA ATA GGT GGT CTC TTC ATC CGA AAC      151
Gly Ala Phe Pro Ser Ser Val Gln Ile Gly Gly Leu Phe Ile Arg Asn
 1           5                  10                      15

ACA GAT CAG GAA TAC ACT GCT TTT CGA TTA GCA ATT TTT CTT CAT AAC      199
Thr Asp Gln Glu Tyr Thr Ala Phe Arg Leu Ala Ile Phe Leu His Asn
             20                      25                      30

ACC GCC CCC AAT GCG TCG GAA GCT CCT TTT AAT TTG GTA CCT CAT GTG      247
Thr Ala Pro Asn Ala Ser Glu Ala Pro Phe Asn Leu Val Pro His Val
                 35                      40                      45

GAC AAC ATT GAG ACA GCC AAC AGT TTT GCT GTA ACA AAC GCC TTC TGT      295
Asp Asn Ile Glu Thr Ala Asn Ser Phe Ala Val Thr Asn Ala Phe Cys
         50                      55                      60

TCC CAG TAT TCT AGA GGA GTA TTT GCC ATT TTT GGA CTC TAT GAT AAG      343
Ser Gln Tyr Ser Arg Gly Val Phe Ala Ile Phe Gly Leu Tyr Asp Lys
     65                      70                      75

AGG TCG GTA CAT ACC TTG ACC TCA TTC TGC AGC GCC TTA CAT ATC TCC      391
Arg Ser Val His Thr Leu Thr Ser Phe Cys Ser Ala Leu His Ile Ser
 80                      85                      90                  95

CTC ATC ACA CCA AGT TTC CCT ACT GAG GGG GAG AGC CAG TTT GTG CTG      439
Leu Ile Thr Pro Ser Phe Pro Thr Glu Gly Glu Ser Gln Phe Val Leu
             100                     105                     110

CAA CTA AGA CCT TCG TTA CGA GGA GCA CTC TTG AGT TTG CTG GAT CAC      487
Gln Leu Arg Pro Ser Leu Arg Gly Ala Leu Leu Ser Leu Leu Asp His
                 115                     120                     125

TAC GAA TGG AAC TGT TTT GTC TTC CTG TAT GAC ACA GAC AGG GGA TAC      535
Tyr Glu Trp Asn Cys Phe Val Phe Leu Tyr Asp Thr Asp Arg Gly Tyr
             130                     135                     140

TCG ATA CTC CAA GCT ATT ATG GAA AAA GCA GGA CAA AAT GGT TGG CAT      583
Ser Ile Leu Gln Ala Ile Met Glu Lys Ala Gly Gln Asn Gly Trp His
     145                     150                     155

GTC AGC GCT ATA TGT GTG GAA AAT TTT AAT GAT GTC AGC TAT AGG CAA      631
Val Ser Ala Ile Cys Val Glu Asn Phe Asn Asp Val Ser Tyr Arg Gln
160                     165                     170                 175

CTT CTA GAA GAA CTT GAC AGA AGA CAA GAG AAG AAG TTT GTA ATA GAC      679
Leu Leu Glu Glu Leu Asp Arg Arg Gln Glu Lys Lys Phe Val Ile Asp
             180                     185                     190

TGT GAG ATA GAG AGA CTT CAA AAC ATA TTA GAA CAG ATT GTA AGT GTT      727
Cys Glu Ile Glu Arg Leu Gln Asn Ile Leu Glu Gln Ile Val Ser Val
                 195                     200                     205

GGA AAG CAT GTT AAA GGC TAC CAT TAT ATC ATT GCA AAC TTG GGA TTC      775
Gly Lys His Val Lys Gly Tyr His Tyr Ile Ile Ala Asn Leu Gly Phe
             210                     215                     220

AAG GAT ATT TCT CTT GAG AGG TTT ATA CAT GGT GGA GCC AAT GTT ACT      823
Lys Asp Ile Ser Leu Glu Arg Phe Ile His Gly Gly Ala Asn Val Thr
     225                     230                     235

GGA TTC CAG TTG GTG GAT TTT AAT ACA CCC ATG GTA ACC AAA CTA ATG      871
Gly Phe Gln Leu Val Asp Phe Asn Thr Pro Met Val Thr Lys Leu Met
240                     245                     250                 255

GAT CGC TGG AAG AAA CTA GAT CAG AGA GAG TAT CCA GGA TCT GAG ACT      919
Asp Arg Trp Lys Lys Leu Asp Gln Arg Glu Tyr Pro Gly Ser Glu Thr
             260                     265                     270

CCT CCA AAG TAC ACC TCT GCT CTG ACT TAT GAT GGA GTC CTT GTG ATG      967
Pro Pro Lys Tyr Thr Ser Ala Leu Thr Tyr Asp Gly Val Leu Val Met
                 275                     280                     285

GCT GAA ACT TTC CGA AGT CTT AGG AGG CAG AAA ATT GAT ATC TCA AGG     1015
Ala Glu Thr Phe Arg Ser Leu Arg Arg Gln Lys Ile Asp Ile Ser Arg
             290                     295                     300

AGA GGA AAG TCT GGG GAT TGT CTG GCA AAT CCT GCT GCT CCA TGG GGC     1063
Arg Gly Lys Ser Gly Asp Cys Leu Ala Asn Pro Ala Ala Pro Trp Gly
```

```
              305                 310                 315
CAG GGA ATT GAC ATG GAG AGG ACA CTC AAA CAG GTT CGA ATT CAA GGG     1111
Gln Gly Ile Asp Met Glu Arg Thr Leu Lys Gln Val Arg Ile Gln Gly
320                 325                 330                 335

CTG ACA GGG AAT GTT CAG TTT GAC CAC TAT GGA CGT AGA GTC AAT TAC     1159
Leu Thr Gly Asn Val Gln Phe Asp His Tyr Gly Arg Arg Val Asn Tyr
                    340                 345                 350

ACA ATG GAT GTG TTT GAG CTG AAA AGC ACA GGA CCT AGA AAG GTT GGT     1207
Thr Met Asp Val Phe Glu Leu Lys Ser Thr Gly Pro Arg Lys Val Gly
                355                 360                 365

TAC TGG AAT GAT ATG GAT AAG TTA GTC TTG ATT CAA GAT GTA CCA ACT     1255
Tyr Trp Asn Asp Met Asp Lys Leu Val Leu Ile Gln Asp Val Pro Thr
            370                 375                 380

CTT GGC AAT GAC ACA GCT GCT ATT GAG AAC AGA ACA GTG GTT GTA ACC     1303
Leu Gly Asn Asp Thr Ala Ala Ile Glu Asn Arg Thr Val Val Val Thr
        385                 390                 395

ACA ATT ATG GAA TCC CCA TAT GTT ATG TAC AAG AAA AAT CAT GAA ATG     1351
Thr Ile Met Glu Ser Pro Tyr Val Met Tyr Lys Lys Asn His Glu Met
400                 405                 410                 415

TTT GAA GGA AAT GAC AAG TAT GAA GGA TAC TGT GTA GAT TTG GCA TCT     1399
Phe Glu Gly Asn Asp Lys Tyr Glu Gly Tyr Cys Val Asp Leu Ala Ser
                    420                 425                 430

GAA ATT GCA AAA CAT ATT GGT ATC AAG TAT AAA ATT GCC ATT GTC CCT     1447
Glu Ile Ala Lys His Ile Gly Ile Lys Tyr Lys Ile Ala Ile Val Pro
                435                 440                 445

GAT GGA AAA TAT GGA GCA AGG GAT GCA GAC ACA AAA ATC TGG AAT GGG     1495
Asp Gly Lys Tyr Gly Ala Arg Asp Ala Asp Thr Lys Ile Trp Asn Gly
            450                 455                 460

ATG GTA GGA GAA CTT GTT TAT GGG AAA GCA GAG ATT GCT ATT GCC CCT     1543
Met Val Gly Glu Leu Val Tyr Gly Lys Ala Glu Ile Ala Ile Ala Pro
        465                 470                 475

CTG ACA ATC ACT TTG GTA CGA GAG GAG GTC ATT GAC TTT TCT AAG CCC     1591
Leu Thr Ile Thr Leu Val Arg Glu Glu Val Ile Asp Phe Ser Lys Pro
480                 485                 490                 495

TTC ATG AGT TTG GGC ATA TCT ATC ATG ATC AAA AAG CCT CAG AAA TCC     1639
Phe Met Ser Leu Gly Ile Ser Ile Met Ile Lys Lys Pro Gln Lys Ser
                    500                 505                 510

AAA CCA GGA GTG TTT TCC TTC TTG GAT CCT CTG GCC TAT GAG ATT TGG     1687
Lys Pro Gly Val Phe Ser Phe Leu Asp Pro Leu Ala Tyr Glu Ile Trp
                515                 520                 525

ATG TGC ATA GTC TTT GCC TAC ATT GGT GTC AGC GTG GTC TTA TTC CTA     1735
Met Cys Ile Val Phe Ala Tyr Ile Gly Val Ser Val Val Leu Phe Leu
            530                 535                 540

GTT AGT AGA TTT AGT CCA TAT GAG TGG CAC ACA GAA GAG CCA GAG GAC     1783
Val Ser Arg Phe Ser Pro Tyr Glu Trp His Thr Glu Glu Pro Glu Asp
        545                 550                 555

GGA AAG GAA GGA CCC AGC GAC CAG CCT CCC AAT GAG TTT GGC ATC TTT     1831
Gly Lys Glu Gly Pro Ser Asp Gln Pro Pro Asn Glu Phe Gly Ile Phe
560                 565                 570                 575

AAC AGC CTC TGG TTT TCC CTG GGT GCT TTT ATG CAG CAA GGA TGT GAC     1879
Asn Ser Leu Trp Phe Ser Leu Gly Ala Phe Met Gln Gln Gly Cys Asp
                    580                 585                 590

ATT TCA CCC AGA TCC CTC TCA GGT CGA ATT GTT GGA GGT GTT TGG TGG     1927
Ile Ser Pro Arg Ser Leu Ser Gly Arg Ile Val Gly Gly Val Trp Trp
                595                 600                 605

TTC TTT ACA CTC ATC ATT ATA TCA TCT TAT ACT GCT AAC CTG GCT GCT     1975
Phe Phe Thr Leu Ile Ile Ile Ser Ser Tyr Thr Ala Asn Leu Ala Ala
            610                 615                 620

TTC CTG ACG GTT GAG CGA ATG GTC TCT CCC ATA GAA AGT GCA GAA GAC     2023
```

```
                                                             -continued

Phe Leu Thr Val Glu Arg Met Val Ser Pro Ile Glu Ser Ala Glu Asp
    625                 630                 635

CTG GCC AAA CAA ACA GAA ATT GCC TAT GGA ACA CTG GAT TCA GGA TCA    2071
Leu Ala Lys Gln Thr Glu Ile Ala Tyr Gly Thr Leu Asp Ser Gly Ser
640                 645                 650                 655

ACA AAA GAA TTC TTC AGA AGA TCA AAA ATA GCA GTG TAT GAA AAG ATG    2119
Thr Lys Glu Phe Phe Arg Arg Ser Lys Ile Ala Val Tyr Glu Lys Met
                660                 665                 670

TGG ACC TAC ATG CGA TCA GCA GAG CCA TCA GTA TTC ACT AGG ACT ACA    2167
Trp Thr Tyr Met Arg Ser Ala Glu Pro Ser Val Phe Thr Arg Thr Thr
            675                 680                 685

GCT GAG GGA GTA GCT CGT GTC CGC AAA TCC AAG GGC AAA TTT GCC TTT    2215
Ala Glu Gly Val Ala Arg Val Arg Lys Ser Lys Gly Lys Phe Ala Phe
        690                 695                 700

CTC CTG GAG TCC ACT ATG AAT GAT AAC ATT GAG CAG CGA AAG CCA TGT    2263
Leu Leu Glu Ser Thr Met Asn Asp Asn Ile Glu Gln Arg Lys Pro Cys
    705                 710                 715

GAC ACG ATG AAA GTG GGA GGA AAT CTG GAT TCC AAA GGC TAT GGA GTA    2311
Asp Thr Met Lys Val Gly Gly Asn Leu Asp Ser Lys Gly Tyr Gly Val
720                 725                 730                 735

GCA ACG CCC AAG GGT TCC TCA TTA AGA ACT CCT GTA AAC CTT GCC GTT    2359
Ala Thr Pro Lys Gly Ser Ser Leu Arg Thr Pro Val Asn Leu Ala Val
                740                 745                 750

TTG AAA CTC AGT GAG GCA GGC GTC TTA GAC AAG CTG AAA AAC AAA TGG    2407
Leu Lys Leu Ser Glu Ala Gly Val Leu Asp Lys Leu Lys Asn Lys Trp
            755                 760                 765

TGG TAC GAT AAA GGT GAA TGT GGA CCC AAA GAC TCT GGA AGC AAG GAC    2455
Trp Tyr Asp Lys Gly Glu Cys Gly Pro Lys Asp Ser Gly Ser Lys Asp
        770                 775                 780

AAG ACG AGT GCC TTG AGC CTG AGC AAT GTA GCA GGC GTC TTC TAC ATT    2503
Lys Thr Ser Ala Leu Ser Leu Ser Asn Val Ala Gly Val Phe Tyr Ile
    785                 790                 795

CTG GTT GGC GGC TTG GGC TTG GCA ATG CTG GTG GCT TTG ATA GAG TTC    2551
Leu Val Gly Gly Leu Gly Leu Ala Met Leu Val Ala Leu Ile Glu Phe
800                 805                 810                 815

TGT TAC AAG TCC AGG GCA GAA GCG AAG AGA ATG AAG CTG ACC TTT TCT    2599
Cys Tyr Lys Ser Arg Ala Glu Ala Lys Arg Met Lys Leu Thr Phe Ser
                820                 825                 830

GAA GCC ATA AGA AAC AAA GCC AGA TTA TCC ATC ACT GGG AGT GTG GGA    2647
Glu Ala Ile Arg Asn Lys Ala Arg Leu Ser Ile Thr Gly Ser Val Gly
            835                 840                 845

GAG AAT GGC CGC GTC TTG ACG CCT GAC TGC CCA AAG GCT GTA CAC ACT    2695
Glu Asn Gly Arg Val Leu Thr Pro Asp Cys Pro Lys Ala Val His Thr
        850                 855                 860

GGA ACT GCA ATC AGA CAA AGT TCA GGA TTG GCT GTC ATT GCA TCG GAC    2743
Gly Thr Ala Ile Arg Gln Ser Ser Gly Leu Ala Val Ile Ala Ser Asp
    865                 870                 875

CTA CCA TAAAACCAA AAAAATAATT GAGTGCCTTA ATTAAACTGT TGGTGACTGG       2799
Leu Pro
880

TGGAAACGCA GCCCTGAGGG ACAGCCACGC GCGGGTCTTT GCTAAACCAA TCCTTTGGCT   2859

GAGAGCGGGA AGTCCGTCCT AACGCGCTGG CCGGACATCA GCAGCAGCAA CGTGTGCATG   2919

AGCTCAGCTC GGAAACCCAA ACTCAGATTT TATATCAGGA AAACTCACAA TTGAGGTTTT   2979

TTTCGGGGAG TGGGTGGGGG AGGGATCTGG GATGGGTGTA TTAACAGCAA CAAATTTCAT   3039

TCGAGTGGAC TCAAAAACTA ATCAGACTTA TGAGTTAGCG CATTAAACTG TGAAGTTCTT   3099

GCTCAGAAAG GCCTTTGTCT TCACCGGAAA GGATAAAATA GTTGTAGAAG TCCGTGAACA   3159
```

```
TGCTAACCTG TGTCTCCAGA ACATCCATAT AGTCCATGGA AGAAAATCCA GCTGAGAAAA    3219

CAAATCACTA AACTGTGATA AGAAAATAAT GAACAAACAT GTAAAACCTG TGGGAAAAAA    3279

AAAATAAAGG AAGTATGTAC ACTTACTTTG GAGAAAACAA ATACTGAAAC ATGCTTGCTT    3339

TTTAACTGAC GTAAATTCAG TAGAGGACAA CACAATTCTT TTTTCTAACC ATCTTAGGGA    3399

ACAATACATT GCAATAATTG ATATAAATGC CATCACTGTA ATAAACTTTA GAGACTTTTT    3459

TTTATAAAAG TTGTTGGTCA TCTTCTTGTT TGCTGTAACC TTCACTATGT CACATGAGTC    3519

GATTCACCGA TTGCATTTGT CTCACAACCA GGAAGAAAAG CAAAAGGAAG AAAACGTTTA    3579

GGTTCAATCA TCAGTCTGCG GTGTAGACTC GAAAGAGATG ACAGGTCACT CATGTTAATG    3639

GTATTATTTA TAATCTCATT CTGTGTACAA CATTGTGGTT TTTGTACCCA CCAAAAAGAA    3699

TAAAACAGCA GATGTTCTTA CAATATCTAC AGAGCTTAAA AGTTTTTCT TATCGTTATA     3759

AAAGTTATTT GAGAAATTAT AAGACTATAA GAGAGATTGT ATTAGTGGTG GGCCATAGTG    3819

GAAAATGTAG CTAGCCCTCA TTATTTTTTG CATACTAAGC TACCCTCCT TTTCAGATCT     3879

TTGACTCATT AACAGATTAA ACTGTCAAAG ATGGAGTCTT TGAGTTGGGG AATGAATCAC    3939

TGTCGGAATT CCATCTTTGG ACACCTGAAG AAAATCAAGC TT                       3981
```

(2) INFORMATION FOR SEQ ID NO:2:

(i) SEQUENCE CHARACTERISTICS:
        (A) LENGTH: 902 amino acids
        (B) TYPE: amino acid
        (D) TOPOLOGY: linear (ii) MOLECULE TYPE: protein (xi) SEQUENCE DESCRIPTION: SEQ ID NO:2:

```
Met Arg Ile Ile Ser Arg Gln Ile Val Leu Leu Phe Ser Gly Phe Trp
-21 -20          -15                 -10

Gly Leu Ala Met Gly Ala Phe Pro Ser Ser Val Gln Ile Gly Gly Leu
 -5              1               5                   10

Phe Ile Arg Asn Thr Asp Gln Glu Tyr Thr Ala Phe Arg Leu Ala Ile
            15                  20                  25

Phe Leu His Asn Thr Ala Pro Asn Ala Ser Glu Ala Pro Phe Asn Leu
            30                  35                  40

Val Pro His Val Asp Asn Ile Glu Thr Ala Asn Ser Phe Ala Val Thr
            45                  50                  55

Asn Ala Phe Cys Ser Gln Tyr Ser Arg Gly Val Phe Ala Ile Phe Gly
 60             65                  70                  75

Leu Tyr Asp Lys Arg Ser Val His Thr Leu Thr Ser Phe Cys Ser Ala
            80                  85                  90

Leu His Ile Ser Leu Ile Thr Pro Ser Phe Pro Thr Glu Gly Glu Ser
            95                  100                 105

Gln Phe Val Leu Gln Leu Arg Pro Ser Leu Arg Gly Ala Leu Leu Ser
            110                 115                 120

Leu Leu Asp His Tyr Glu Trp Asn Cys Phe Val Phe Leu Tyr Asp Thr
            125                 130                 135

Asp Arg Gly Tyr Ser Ile Leu Gln Ala Ile Met Glu Lys Ala Gly Gln
140             145                 150                 155

Asn Gly Trp His Val Ser Ala Ile Cys Val Glu Asn Phe Asn Asp Val
                160                 165                 170

Ser Tyr Arg Gln Leu Leu Glu Glu Leu Asp Arg Arg Gln Glu Lys Lys
            175                 180                 185
```

```
Phe Val Ile Asp Cys Glu Ile Glu Arg Leu Gln Asn Ile Leu Glu Gln
        190                 195                 200

Ile Val Ser Val Gly Lys His Val Lys Gly Tyr His Tyr Ile Ile Ala
        205                 210                 215

Asn Leu Gly Phe Lys Asp Ile Ser Leu Glu Arg Phe Ile His Gly Gly
220                 225                 230                 235

Ala Asn Val Thr Gly Phe Gln Leu Val Asp Phe Asn Thr Pro Met Val
            240                 245                 250

Thr Lys Leu Met Asp Arg Trp Lys Lys Leu Asp Gln Arg Glu Tyr Pro
            255                 260                 265

Gly Ser Glu Thr Pro Pro Lys Tyr Thr Ser Ala Leu Thr Tyr Asp Gly
            270                 275                 280

Val Leu Val Met Ala Glu Thr Phe Arg Ser Leu Arg Arg Gln Lys Ile
            285                 290                 295

Asp Ile Ser Arg Arg Gly Lys Ser Gly Asp Cys Leu Ala Asn Pro Ala
300                 305                 310                 315

Ala Pro Trp Gly Gln Gly Ile Asp Met Glu Arg Thr Leu Lys Gln Val
            320                 325                 330

Arg Ile Gln Gly Leu Thr Gly Asn Val Gln Phe Asp His Tyr Gly Arg
            335                 340                 345

Arg Val Asn Tyr Thr Met Asp Val Phe Glu Leu Lys Ser Thr Gly Pro
            350                 355                 360

Arg Lys Val Gly Tyr Trp Asn Asp Met Asp Lys Leu Val Leu Ile Gln
            365                 370                 375

Asp Val Pro Thr Leu Gly Asn Asp Thr Ala Ala Ile Glu Asn Arg Thr
380                 385                 390                 395

Val Val Val Thr Thr Ile Met Glu Ser Pro Tyr Val Met Tyr Lys Lys
                    400                 405                 410

Asn His Glu Met Phe Glu Gly Asn Asp Lys Tyr Glu Gly Tyr Cys Val
            415                 420                 425

Asp Leu Ala Ser Glu Ile Ala Lys His Ile Gly Ile Lys Tyr Lys Ile
            430                 435                 440

Ala Ile Val Pro Asp Gly Lys Tyr Gly Ala Arg Asp Ala Asp Thr Lys
445                 450                 455

Ile Trp Asn Gly Met Val Gly Glu Leu Val Tyr Gly Lys Ala Glu Ile
460                 465                 470                 475

Ala Ile Ala Pro Leu Thr Ile Thr Leu Val Arg Glu Glu Val Ile Asp
            480                 485                 490

Phe Ser Lys Pro Phe Met Ser Leu Gly Ile Ser Ile Met Ile Lys Lys
            495                 500                 505

Pro Gln Lys Ser Lys Pro Gly Val Phe Ser Phe Leu Asp Pro Leu Ala
        510                 515                 520

Tyr Glu Ile Trp Met Cys Ile Val Phe Ala Tyr Ile Gly Val Ser Val
            525                 530                 535

Val Leu Phe Leu Val Ser Arg Phe Ser Pro Tyr Glu Trp His Thr Glu
540                 545                 550                 555

Glu Pro Glu Asp Gly Lys Glu Gly Pro Ser Asp Gln Pro Pro Asn Glu
            560                 565                 570

Phe Gly Ile Phe Asn Ser Leu Trp Phe Ser Leu Gly Ala Phe Met Gln
            575                 580                 585

Gln Gly Cys Asp Ile Ser Pro Arg Ser Leu Ser Gly Arg Ile Val Gly
            590                 595                 600

Gly Val Trp Trp Phe Phe Thr Leu Ile Ile Ile Ser Ser Tyr Thr Ala
```

```
              605                 610                 615
Asn Leu Ala Ala Phe Leu Thr Val Glu Arg Met Val Ser Pro Ile Glu
620                 625                 630                 635

Ser Ala Glu Asp Leu Ala Lys Gln Thr Glu Ile Ala Tyr Gly Thr Leu
                640                 645                 650

Asp Ser Gly Ser Thr Lys Glu Phe Phe Arg Arg Ser Lys Ile Ala Val
                655                 660                 665

Tyr Glu Lys Met Trp Thr Tyr Met Arg Ser Ala Glu Pro Ser Val Phe
                670                 675                 680

Thr Arg Thr Thr Ala Glu Gly Val Ala Arg Val Arg Lys Ser Lys Gly
                685                 690                 695

Lys Phe Ala Phe Leu Leu Glu Ser Thr Met Asn Asp Asn Ile Glu Gln
700                 705                 710                 715

Arg Lys Pro Cys Asp Thr Met Lys Val Gly Gly Asn Leu Asp Ser Lys
                720                 725                 730

Gly Tyr Gly Val Ala Thr Pro Lys Gly Ser Ser Leu Arg Thr Pro Val
                735                 740                 745

Asn Leu Ala Val Leu Lys Leu Ser Glu Ala Gly Val Leu Asp Lys Leu
                750                 755                 760

Lys Asn Lys Trp Trp Tyr Asp Lys Gly Glu Cys Gly Pro Lys Asp Ser
765                 770                 775

Gly Ser Lys Asp Lys Thr Ser Ala Leu Ser Leu Ser Asn Val Ala Gly
780                 785                 790                 795

Val Phe Tyr Ile Leu Val Gly Gly Leu Gly Leu Ala Met Leu Val Ala
                800                 805                 810

Leu Ile Glu Phe Cys Tyr Lys Ser Arg Ala Glu Ala Lys Arg Met Lys
                815                 820                 825

Leu Thr Phe Ser Glu Ala Ile Arg Asn Lys Ala Arg Leu Ser Ile Thr
                830                 835                 840

Gly Ser Val Gly Glu Asn Gly Arg Val Leu Thr Pro Asp Cys Pro Lys
845                 850                 855

Ala Val His Thr Gly Thr Ala Ile Arg Gln Ser Ser Gly Leu Ala Val
860                 865                 870                 875

Ile Ala Ser Asp Leu Pro
                880

(2) INFORMATION FOR SEQ ID NO:3:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:3:

ATGCATCGGA AGCTCCTTTC AATTTGGTAC CTCATGTGGA                    40

(2) INFORMATION FOR SEQ ID NO:4:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:4:

AGTGTGGGAG AAAACGGCCG TGTGCTGACC CCTGACTGCC                    40
```

AMPA-BINDING HUMAN GLUR4 RECEPTORS

This application is a divisional of application Ser. No. 08/259,164, filed Jun. 13, 1994, now U.S. Pat. No. 5,643,785, which is a continuation of application Ser. No. 07/924,553, filed Aug. 5, 1992 now abandoned.

FIELD OF THE INVENTION

This invention is concerned with applications of recombinant DNA technology in the field of neurobiology. More particularly, the invention relates to the cloning and expression of DNA coding for excitatory amino acid (EAA) receptors, especially human EAA receptors,

BACKGROUND TO THE INVENTION

In the mammalian central nervous system (CNS), the transmission of nerve impluses is controlled by the Interaction between a neurotransmitter substance released by the "sending" neuron which binds to a surface receptor on the "receiving" neuron, to cause excitation thereof. L-glutamate is the most abundant neurotransmitter in the CNS, and mediates the major excitatory pathway in vertebrates. Glutamate is therefore referred to as an excitatory amino acid (EAA) and the receptors which respond to it are variously referred to as glutamate receptors, or more commonly as EAA receptors.

Using tissues isolated from mammalian brain, and various synthetic EAA receptor agonists, knowledge of EAA receptor pharmacology has been refined somewhat. Members of the EAA receptor family are now grouped into three main types based on differential binding to such agonists. One type of EAA receptor, which in addition to glutamate also binds the agonist NMDA (N-methyl-D-aspartate), is referred to as the NMDA type of EAA receptor. Two other glutamate-binding types of EAA receptor, which do not bind NMDA, are named according to their preference for binding with two other EAA receptor agonists, namely AMPA (alpha-amino-3-hydroxy-5-methyl-isoxazole-4-proplonate) and kainate. Particularly, receptors which bind glutamate but not NMDA, and which bind with greater affinity to kainate than to AMPA, are referred to as kainate type EAA receptors. Similarly, those EAA receptors which bind glutamate but not NMDA, and which bind AMPA with greater affinity than kainate are referred to as AMPA type EAA receptors.

The glutamate-binding EAA receptor family is of great physiological and medical importance. Glutamate is involved in many aspects of long-term potentiation (learning and memory), in the development of synaptic plasticity, in epileptic seizures, in neuronal damage caused by ischemia following stroke or other hypoxic events, as well as in other forms of neurodegenerative processes. However, the development of therapeutics which modulate these processes has been very difficult, due to the lack of any homogeneous source of receptor material with which to discover selectively binding drug molecules, which interact specifically at the interface of the EAA receptor. The brain derived tissues currently used to screen candidate drugs are heterogeneous receptor sources, possessing on their surface many receptor types which interfere with studies of the EAA receptor/ligand interface of interest. The search for human therapeutics is further complicated by the limited availability of brain tissue of human origin. It would therefore be desirable to obtain cells that are genetically engineered to produce only the receptor of interest. With cell lines expressing cloned receptor genes, a substrate which is homogeneous for the desired receptor is provided, for drug screening programs.

Very recently, genes encoding substituent polypeptides of EAA receptors from non-human sources, principally rat, have been discovered. Holimann et al., Nature 342: 643, 1989 described the isolation from rat of a gene referred to originally as GluR-K1 (but now called simply GluR1). This gene encodes a member of the rat EAA receptor family, and was originally suspected as being of the kainate type. Subsequent studies by Keinanen et al., Science 249: 556, 1990, showed, again in rat, that a gene called GluR-A, which was in fact identical to the previously isolated GluR1, in fact encodes a receptor not of the kainate type, but rather of the AMPA type. These two groups of researchers have since reported as many as five related genes isolated from rat sources. Boulter et al., Science 249: 1033, 1990, revealed that, in addition to GluR1, the rat contained 3 other related genes, which they called GluR2, GluR3, and GluR4, and Bettler et al., Neuron 5: 583, 1990 described GluR5. Keinanen et al., supra, described genes called GluR-A, GluR-B, GluR-C and GluR-D which correspond precisely to GluR1, GluR2, GluR3 and GluR4 respectively. Sommer et al., Science 249: 1580, 1990 also showed, for GluR-A, GluR-B, GluR-C and GluR-D two alternatively spliced forms for each gone. These authors, as well as Monyar et al., Neuron 6: 799, 1991 were able to show that the differently spliced versions of these genes were differentially expressed in the rat brain. In addition to the isolation of these AMPA receptor genes, several studies have more recently attempted to determine the ion-gating properties of different mixtures of the known receptors (Nakanishi et al., Neuron 5: 569, 1990; Hollmann et al., Science 252: 851, 1991; Verdoorn et al., Science 252: 1715, 1991; and see WO 91/06648).

There has emerged from these molecular cloning advances a better understanding of the structural features of EAA receptors and their subunits, as they exist in the rat brain. According to the current model of EAA receptor structure, each is heteromeric in structure, consisting of individual membrane-anchored subunits, each having four transmembrane regions, and extracellular domains that dictate ligand binding properties to some extent and contribute to the ion-gating function served by the receptor complex. Keinanen et al, supra, have shown for example that each subunit of the rat GluR receptor, including those designated GluR-A, GluR-8, GluR-C and GluR-D, display cation channel activity gated by glutamate, by AMPA and by kainate, in their unitary state. When expressed in combination however, for example GluR-A in combination with GluR-B, gated ion channels with notably larger currents are produced by the host mammalian cells.

In the search for therapeutics useful to treat CNS disorders in humans, it is highly desirable of course to provide a screen for candidate compounds that is more representative of the human situation than is possible with the rat receptors isolated to date. It is particularly desirable to provide cloned genes coding for human receptors, and cell lines expressing those genes, in order to generate a proper screen for human therapeutic compounds. These, accordingly, are objects of the present invention.

SUMMARY OF THE INVENTION

The present invention provides an isolated polynucleotide that codes for an AMPA-binding human EAA receptor. By providing polynucleotide that codes specifically for a CNS receptor native to humans, the present invention provides means for evaluating the human nervous system, and particularly for assessing potentially therapeutic interactions between the AMPA-binding human EAA receptors and selected natural and synthetic ligands.

In one of Its aspects, the present invention provides an isolated polynucleotide comprising nucleic acids arranged in a sequence that codes for a human EAA receptor herein designated the human GluR4B receptor. Alternatively, the polynucleotide may code for an AMPA-binding fragment of the human GluR4B receptor, or for an AMPA-binding variant of the human GluR4B receptor. In various specific embodiments of the present invention, the polynucleotide consists of DNA e.g. cDNA, or of RNA e.g. messenger RNA. In other embodiments of the present invention, the polynucleotide may be coupled to a reporter molecule, such as a radioactive label, for use in autoradiographic studies of human GluR4B receptor tissue distribution. In further embodiments of the present invention, fragments of the polynucleotides of the invention, including radiolabelled versions thereof, may be employed either as probes for detection of glutamate receptor-encoding polynucleotides, as primers appropriate for amplifying such polynucleotides present in a biological specimen, or as templates for expression of the human GluR4B receptor or an AMPA-binding fragment of variant thereof.

According to another aspect of the present invention, there is provided a cellular host having Incorporated therein a polynucleotide of the present invention. In embodiments of the present invention, the polynucleotide is a DNA molecule and is incorporated for expression and secretion in the cellular host, to yield a functional, membrane-bound human GluR4B receptor or to yield an AMPA-binding fragment or variant of the human GluR4B receptor. In other embodiments of the present invention, the polynucleotide is an RNA molecule which is incorporated in the cellular host to yield the human GluR4B receptor as a functional, membrane bound product of translation.

According to another aspect of the invention, there is provided a process for obtaining a substantially homogeneous source of a human EAA receptor useful for performing ligand binding assays, which comprises the steps of culturing a genetically engineered cellular host of the invention, and then recovering the cultured cells. Optionally, the cultured calls may be treated to obtain membrane preparations thereof, for use in the ligand binding assays.

According to another aspect of the present invention, there is provided a method for assessing the binding interaction between a test compound and a human CNS receptor, which comprises the steps of incubating the test compound under appropriate conditions with a human GluR4B receptor source, i.e., a cellular host of the invention or a membrane preparation derived therefrom, and then determining the extent or result of binding between the substance and the receptor source.

These and other aspects of the invention are now described in greater detail with reference to the accompanying drawings, in which:

BRIEF REFERENCE TO THE DRAWINGS

FIGS. 1A–1G provide a DNA sequence (SEQ ID NO:1) coding for the human GluR4B receptor, and the amino acid (SEQ ID NO:2) sequence thereof;

FIG. 4 illustrates the AMPA-binding property of the human GluR4B receptor.

DETAILED DESCRIPTION OF THE INVENTION AND ITS PREFERRED EMBODIMENTS

Figure 2:
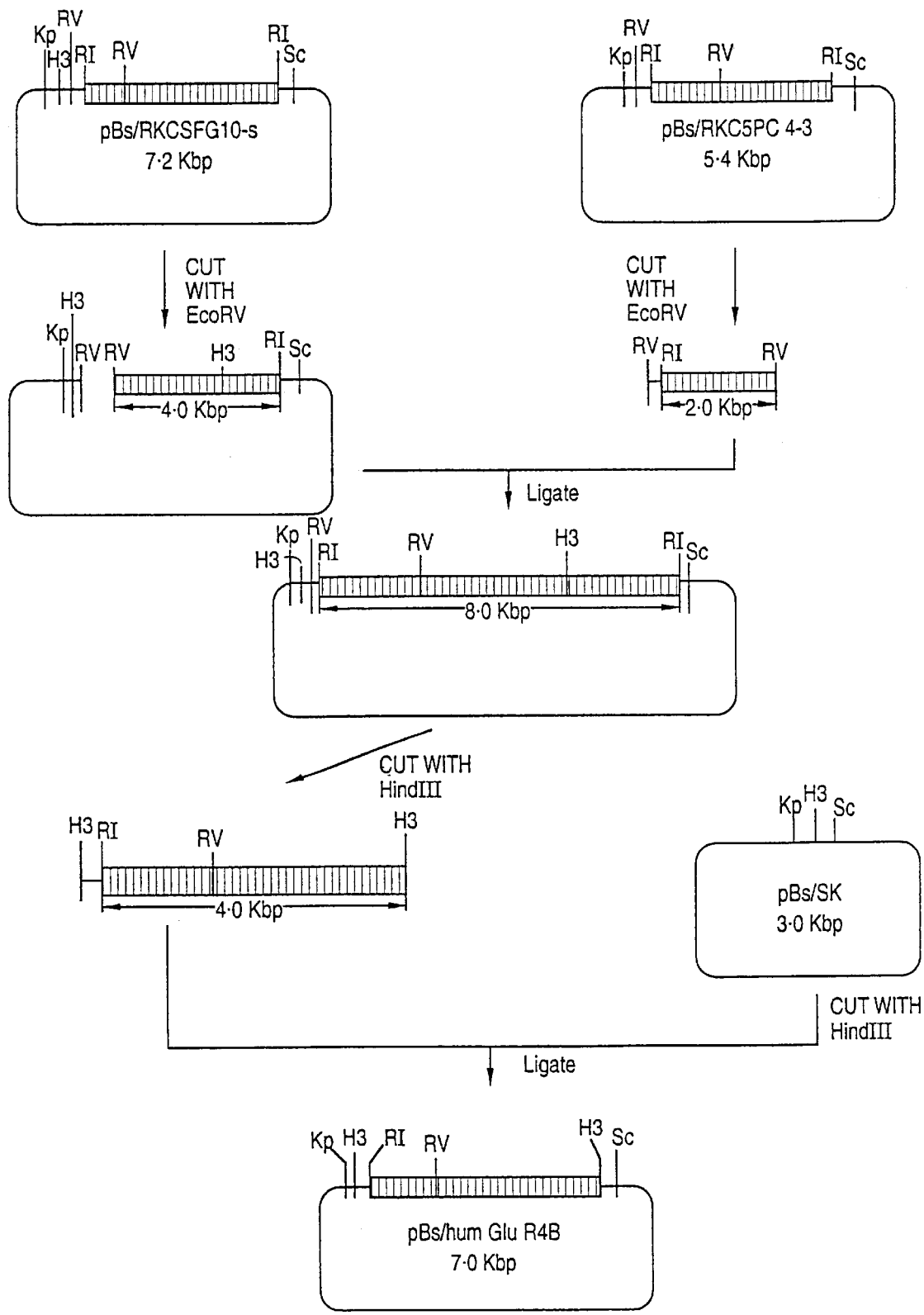
FIG. 2 depicts the strategy employed in cloning the DNA sequence provided in FIGS. 1A–1G, where Sc is SacI, RI is EcoRI, RV is EcoRV, Kp is KpnI and H3 is HindIII.

The invention relates to human CNS receptors of the AMPA-binding type, and provides isolated polynucleotides that code for such receptors. The term "isolated" is used herein with reference to intact polynucleotides that are generally less than about 4,000 nucleotides in length and which are otherwise isolated from DNA coding for other human proteins.

In the present context, human CNS receptors of the AMPA-binding type exhibit a characteristic ligand binding profile, which reveals glutamate binding and relative greater affinity for binding AMPA than for other binding other CNS receptor ligands such as kainate, glutamate and their closely related analogues.

In the present specification, an AMPA-binding receptor is said to be "functional" if a cellular host producing it exhibits de novo channel activity when exposed appropriately to AMPA, as determined by the established electrophysiological assays described for example by Hollman et al, supra, or by any other assay appropriate for detecting conductance across a cell membrane.

The human GluR4B receptor of the invention possess structural features characteristic of the EAA receptors in general, including extracellular N- and C-terminal regions, as well as four internal hydrophobic domains which serve to anchor the receptor within the cell surface membrane. More specifically, GluR4B receptor is a protein characterized structurally as a single polypeptide chain that is produced initially in precursor form bearing an 21 amino acid residue N-terminal signal peptide, and is transported to the cell surface in mature form, lacking the signal peptide and consisting of 881 amino acids arranged in the sequence illustrated, by single letter code, in FIG. 1 and SEQ ID NO:1 and 2. Unless otherwise stated, the term human GluR4B receptor refers to the mature form of the receptor, and amino acid residues of the human GluR4B receptor are accordingly numbered with reference to the mature protein sequence. With respect to structural domains of the receptor, hydropathy analysis reveals four putative transmembrane domains, one spanning residues 526–545 inclusive (TM-1), another spanning residues 572–590 (TM-2), a third spanning residues 601–819 (TM-3) and the fourth spanning residues 793–813 (TM-4). Based on this assignment, it is likely that the human GluR4B receptor structure, in Its natural membrane-bound form, consists of a 525 amino acid N-terminal extracellular domain, followed by a hydrophobic region containing four transmembrane domains and an extracellular, 68 amino acid C-terminal domain.

Binding assays performed with various ligands, and with membrane preparations derived from mammalian cells engineered genetically to produce the human GluR4B receptor in membrane-bound form indicate that GluR4B binds selectively to AMPA, relative particularly to kainate and NMDA. This feature, coupled with the medically significant connection between AMPA-type receptors and neurological disorders and disease indicate that the present receptor, and its AMPA-binding fragments and variants, will serve as valuable tools in the screening and discovery of ligands useful to modulate in vivo interactions between such receptors and their natural ligand, glutamate. Thus, a key aspect of the present invention resides in the construction of cells that are engineered genetically to produce human GluR4B receptor, to serve as a ready and homogeneous source of receptor for use in in vitro ligand binding and/or channel activation assays.

For use in the ligand binding assays, it is desirable to construct by application of genetic engineering techniques a mammalian cell that produces a human GluR4B receptor as a heterologous, membrane-bound product. According to one embodiment of the invention, the construction of such engineered cells is achieved by introducing into a selected host cell a recombinant DNA secretion construct in which DNA coding for a secretable form of the human GluR4B receptor i.e., a form of the receptor bearing its native signal peptide or a functional, heterologous equivalent thereof, is linked operably with expression controlling elements that are functional in the selected host to drive expression of the receptor-encoding DNA, and thus elaborate the receptor protein in its desired, mature and membrane-bound form. Such cells are herein characterized as having the receptor-encoding DNA incorporated "expressibly" therein. The receptor-encoding DNA is referred to as "heterologous" with respect to the particular cellular host if such DNA is not naturally found in the particular host. The particular cell type selected to serve as host for production of the human GluR4B receptor can be any of several call types currently available in the art, but should not of course be a call type that in its natural state elaborates a surface receptor that can bind excitatory amino acids, and so confuse the assay results sought from the engineered cell line. Generally, such problems are avoided by selecting as host a non-neuronal cell type, and can further be avoided using non-human cell lines, as is conventional. It will be appreciated that neuronal- and human-type cells may nevertheless serve as expression hosts, provided that "background" binding to the test ligand is accounted for in the assay results.

According to one embodiment of the present invention, the cell line selected to serve as host for human GluR4B receptor production is a mammalian cell. Several types of such cell lines are currently available for genetic engineering work, and these include the chinese hamster ovary (CHO) calls for example of K1 lineage (ATCC CCL 61) including the Pro5 variant (ATCC CRL 1281); the fibroblast-like cells derived from SV40-transformed African Green monkey kidney of the CV-1 lineage (ATCC CCL 70), of the COS-1 lineage (ATCC CRL 1 650) and of the COS-7 lineage (ATCC CRL 1651); murine L-cells, murine 3T3 cells (ATCC CRL 1658), murine C127 cells, human embryonic kidney cells of the 293 lineage (ATCC CRL 1573), human carcinoma cells including those of the HeLa lineage (ATCC CCL 2), and neuroblastoma cells of the lines IMR-32 (ATCC CCL 127), SK-N-MC (ATCC HTB 10) and SK-N-SH (ATCC HTB 11).

A variety of gene expression systems have been adapted for use with these hosts and are now commercially available, and any one of these systems can be selected to drive expression of the receptor-encoding DNA. These systems, available typically in the form of plasmidic vectors, incorporate expression cassettes the functional components of which include DNA constituting expression controlling sequences, which are host-recognized and enable expression of the receptor-encoding DNA when linked 5' thereof, The systems further incorporate DNA sequences which terminate expression when linked 3' of the receptor-encoding region. Thus, for expression in the selected mammalian cell host, there is generated a recombinant DNA expression construct in which DNA coding for the receptor in secretable form is linked with expression controlling DNA sequences recognized by the host, and which include a region 5' of the receptor-encoding DNA to drive expression, and a 3' region to terminate expression. The plasmidic vector harbouring the recombinant DNA expression construct typically incorporates such other functional components as an origin of replication, usually virally-derived, to permit replication of the plasmid in the expression host and desirably also for plasmid amplification in a bacterial host, such as *E. coli*. To provide a marker enabling selection of stably transformed recombinant calls, the vector will also incorporate a gene conferring some survival advantage on the transformants, such as a gene coding for neomycin resistance in which case the transformants are plated in medium supplemented with neomycin.

Included among the various recombinant DNA expression systems that can be used to achieve mammalian call expression of the receptor-encoding DNA are those that exploit promoters of viruses that infect mammalian cells, such as the promoter from the cytomegalovirus (CMV), the Rous sarcoma virus (RSV), simian virus (SV40), murine mammary tumor virus (MMTV) and others. Also useful to drive expression are promoters such as the LTR of retroviruses, insect cell promoters such as those regulated by temperature, and isolated from Drosophila, as well as mammalian gene promoters such as those regulated by heavy metals i.e.the metalothionein gene promoter, and other steroid-inducible promoters.

For incorporation into the recombinant DNA expression vector, DNA coding for the human GluR4B receptor, or an AMPA-binding fragment or variant thereof, can be obtained by applying selected techniques of gene isolation or gene synthesis. As described in more detail in the examples herein, the human GluR4B receptor is encoded within the genome of human brain tissue, and can therefore be obtained from human DNA libraries by careful application of conventional gene isolation and cloning techniques. This typically will entail extraction of total messenger RNA from a fresh source of human brain tissue, preferably cerebellum or hippocampus tissue, followed by conversion of message to cDNA and formation of a library in for example a bacterial plasmid, more typically a bacteriophage. Such bacteriophage harbouring fragments of the human DNA are typically grown by plating on a lawn of susceptible *E. coil* bacteria, such that individual phage plaques or colonies can be isolated. The DNA carried by the phage colony is then typically immobilized on a nitrocellulose or nylon-based hybridization membrane, and then hybridized, under carefully controlled conditions, to a radioactively (or otherwise) labelled oligonucleotide probe of appropriate sequence to identify the particular phage colony carrying receptor-encoding DNA or fragment thereof. Typically, the gone or a portion thereof so identified is subcloned into a plasmidic vector for nucleic acid sequence analysis.

In a specific embodiment of the invention, the GluR4B receptor is encoded by the DNA sequence illustrated in FIGS. 1A–1G. In an alternative, the DNA sequences coding for the selected receptor may be a synonymous codon equivalent of the illustrated DNA sequences.

The illustrated DNA sequence constitutes the cDNA sequence identified in human brain cDNA libraries in the manner exemplified herein. Having herein provided the nucleotide sequence of the human GluR4B receptor, however, it will be appreciated that polynucleotides encoding the receptor can be obtained by other routes. Automated techniques of gone synthesis and/or amplification can be performed to generate DNA coding therefor. Because of the length of the human GluR4B receptor-encoding DNA, application of automated synthesis may require staged gene construction, in which regions of the gene up to about 300 nucleotides in length are synthesized individually and then ligated in correct succession by overhang complementarity for final assembly. Individually synthesized gene regions can be amplified prior to assembly, using established polymerase chain reaction (PCR) technology.

The application of automated gene synthesis techniques provides an opportunity for generating polynucleotides that encode variants of the naturally occurring human GluR4B receptor, it will be appreciated, for example, that polynucleotides coding for the receptor can be generated by substituting synonymous codons for those represented in the naturally occurring polynucleotide sequences herein identified. In addition, polynucleotides coding for human GluR4B receptor variants can be generated which for example incorporate one or more, e.g. 1 to 10, single amino acid substitutions, deletions or additions. Since it will for the most part be desirable to retain the natural ligand binding profile of the receptor for screening purposes, it is desirable to limit amino acid substitutions, for example to the so-called conservative replacements in which amino acids of like charge are substituted, and to limit substitutions to those sites less critical for receptor activity e.g. within about the first 20 N-terminal residues of the mature receptor, and such other regions as are elucidated upon receptor domain mapping.

With appropriate template DNA in hand, the technique of PCR amplification may also be used to directly generate all or part of the final gene. In this case, primers are synthesized which will prime the PCR amplification of the final product, either in one place, or in several places that may be ligated together. This may be via step-wise ligation of blunt ended, amplified DNA fragments, or preferentially via step-wise ligation of fragments containing naturally occurring restriction endonuclease sites, in this application, it is possible to use either EDNA or genomic DNA as the template for the PCR amplification, in the former case, the cDNA template can be obtained from commercially available or self-constructed cDNA libraries of various human brain tissues, including hippocampus and cerebellum.

Once obtained, the receptor-encoding DNA is incorporated for expression into any suitable expression vector, and host cells are transfected therewith using conventional procedures, such as DNA-mediated transformation, electroporation, or particle gun transformation. Expression vectors may be selected to provide transformed cell lines that express the receptor-encoding DNA either transiently or in a stable manner, For transient expression, host cells are typically transformed with en expression vector harbouring an origin of replication functional in a mammalian cell. For stable expression, such replication origins are unnecessary, but the vectors will typically harbour a gone coding for a product that confers on the transformants a survival advantage, to enable their selection. Genes coding for such selectable markers include the *E. coil* gpt gene which confers resistance to mycophenolic acid, the neo gene from transposon Tn5 which confers resistance to the antibiotic G418 and to neomycin, the dhfr sequence from murine cells or *E. coil* which changes the phenotype of DHFR− cells into DHFR+ calls, and the tk gene of herpes simplex virus, which makes TK− cells phenotypically TK+ calls. Both transient expression and stable expression can provide transformed cell lines, and membrane preparations derived therefrom, for use in ligand screening assays.

For use in screening assays, calls transiently expressing the receptor-encoding DNA can be stored frozen for later use, but because the rapid rate of plasmid replication will lead ultimately to cell death, usually in a few days, the transformed cells should be used as soon as possible. Such assays may be performed either with intact cells, or with membrane preparations derived from such cells. The membrane preparations typically provide a more convenient substrate for the ligand binding experiments, and are therefore preferred as binding substrates. To prepare membrane preparations for screening purposes, i.e., ligand binding experiments, frozen intact cells are Homogenized while in cold water suspension and a membrane pellet is collected after centrifugation. The pellet is then washed in cold water, and dialyzed to remove endogenous EAA ligands such as glutamate, that would otherwise compete for binding in the assays. The dialyzed membranes may then be used as such, or after storage in lyophilized form, in the ligand binding assays. Alternatively, intact, fresh cells harvested about two days after transient transfection or after about the same period following fresh plating of stably transfected cells, can be used for ligand binding assays by the same methods as used for membrane preparations. When cells are used, the cells must be harvested by more gentle centrifugation so as not to damage them, and all washing must be done in a buffered medium, for example in phosphate-buffered saline, to avoid osmotic shock and rupture of the cells.

The binding of a substance, i.e., a candidate ligand, to human GluR4B receptor of the invention is evaluated typically using a predetermined amount of cell-derived membrane (meassured for example by protein determination), generally from about 25 ug to 100 ug. Generally, competitive binding assays will be useful to evaluate the affinity of a test compound relative to AMPA. This competitive binding assay can be performed by incubating the membrane preparation with radiolabelled AMPA, for example [3H]-AMPA, in the presence of unlabelled test compound added at varying concentrations. Following incubation, either displaced or bound radiolabelled AMPA can be recovered and measured, to determine the relative binding affinities of the test compound and AMPA for the particular receptor used as substrate. In this way, the affinities of various compounds for the AMPA-binding human CNS receptors can be measured. Alternatively, a radiolabelled analogue of glutamate may be employed in place of radiolabelled AMPA, as competing ligand.

As an alternative to using cells that express receptor-encoding DNA, ligand-characterization may also be performed using cells for example *Xenopus oocytes*, that yield functional membrane-bound receptor following introduction by injection either of receptor-encoding messenger RNA into the oocyto cytoplasm, or of receptor-encoding DNA into the oocyte nucleus. To generate the messenger RNA of cytoplasmic delivery, the receptor-encoding DNA is typically subcloned first into a plasmidic vector adjacent a suitable promoter region, such as the T3 or T7 bacteriophage promoters, to enable transcription into RNA message. RNA is then transcribed from the inserted gene in vitro, collected and then injected into *Xenopus oocytes*. Following the injection of nL volumes of an RNA solution, the oocytes are left to incubate for up to several days, and are then tested for the ability to respond to a particular ligand molecule supplied in a bathing solution. Since functional EAA receptors act in part by operating a membrane channel through which ions may selectively pass, the functioning of the receptor in response to a particular ligand molecule in the bathing solution may typically be measured as an electrical current utilizing microelectrodes inserted into the cell, in the established manner.

In addition to using the receptor-encoding DNA to construct cell lines useful for ligand screening, expression of the DNA can, according to another aspect of the invention, be performed to produce fragments of the receptor in soluble form, for structure investigation, to raise antibodies and for other experimental uses. It is expected that the portion of the human GluR4B receptor responsible for AMPA-binding resides on the outside of the cell, i.e., is extracellular. It is therefore desirable in the first instance to facilitate the characterization of the receptor-ligand interaction by providing this extracellular ligand-binding domain in quantity and in isolated form, i.e., free from the remainder of the receptor. To accomplish this, the full-length human GluR receptor-encoding DNA may be modified by site-directed mutagenesis, so as to introduce a translational stop codon into the extracellular N-terminal region, immediately before the sequence encoding the first transmembrane domain (TM1), i.e., before residue 526 as shown in FIGS. 1A–1G. Since there will no longer be produced any transmembrane domain(s) to "anchor" the receptor into the membrane, expression of the modified gene will result in the secretion, in soluble form, of only the extracellular ligand-binding domain. Standard ligand-binding assays may then be performed to ascertain the degree of binding of a candidate compound to the extracellular domain so produced. It may of course be necessary, using site-directed mutagenesis, to produce several different versions of the extracellular regions, in order to optimize the degree of ligand binding to the isolated domains.

Alternatively, it may be desirable to produce an extracellular domain of the receptor which is not derived from the amino-terminus of the mature protein, but rather from the carboxy-terminus instead, for example domains immediately following the fourth transmembrane domain (TM4), i.e., residing between amino acid residues 814–881 inclusive (FIGS. 1A–1G). In this case, site-directed mutagenesis and/or PCR-based amplification techniques may readily be used to provide a defined fragment of the gone encoding the receptor domain of interest. Such a DNA sequence may be used to direct the expression of the desired receptor fragment, either intracellularly, or in secreted fashion, provided that the DNA encoding the gene fragment is inserted adjacent to a translation start codon provided by the expression vector, and that the required translation reading frame is carefully conserved.

It will be appreciated that the production of such AMPA-binding fragments of the human GluR4B receptor may be accomplished in a variety of host cells. Mammalian cells such as CHO cells may be used for this purpose, the expression typically being driven by an expression promoter capable of high-level expression, for example the CMV (cytomagalovirus) promoter. Alternately, non-mammalian cells, such as Insect Sf9 (*Spodoptera frugiperda*) cells may be used, with the expression topically being driven by expression promoters of the baculovirus, for example the strong, late polyhedrin protein promoter. Filamentous fungal expression systems may also be used to secrete large quantities of such extracellular domains of the EAA receptor. Aspergillus nidulans, for example, with the expression being driven by the a/cA promoter, would constitute such an acceptable system. In addition to such expression hosts, it will be further appreciated that any prokaryotic or other eukaryotic expression system capable of expressing heterologous genes or gene fragments, whether intracellularly or extracellularly would be similarly acceptable.

For use particularly in detecting the presence and/or location of a human GluR4B receptor, for example in brain tissue, the present invention also provides, in another of Its aspects, labelled antibody to the human GluR4B receptor. To raise such antibodies, there may be used as immunogen either the intact, soluble receptor or an immunogenic fragment thereof i.e. a fragment capable of eliciting an immune response, produced in a microbial or mammalian cell host as described above or by standard peptide synthesis techniques. Regions of human GluR4B receptor particularly suitable for use as immunogenic fragments include those corresponding in sequence to an extracellular region of the receptor, or a portion of the extracellular region, such as peptides consisting of residues 1–525 or a fragment thereof comprising at least about 10 residues, including particularly fragments containing residues 173–188 or 474–517; and peptides corresponding to the region between transmembrane domains TM-2 and TM-3, such as a peptide consisting of residues 591–600. Peptides consisting of the C-terminal domain (residues 814–881), or fragment thereof, may also be used for the raising of antibodies.

The raising of antibodies to the selected human GluR4B receptor or immunogenic fragment can be achieved, for polyclonal antibody production, using immunization protocols of conventional design, and any of a variety of mammalian hosts, such as sheep, goats and rabbits. Alternatively, for monoclonal antibody production, immunocytes such as spienocytes can be recovered from the immunized animal and fused, using hybridoma technology, to a myeloma cells. The fusion products are then screened by culturing in a selection medium, and cells producing antibody are recovered for continuous growth, and antibody recovery. Recovered antibody can then be coupled covalently to a detectable label, such as a radiolabel, enzyme label, luminescent label or the like, using linker technology established for this purpose.

In detectably labelled form, e.g. radiolabelled form, DNA or RNA coding for a human GluR4B receptor, and selected regions thereof, may also be used, in accordance with another aspect of the present invention, as hybridization probes for example to identify sequence-related genes resident in the human or other mammalian genomes (or cDNA libraries) or to locate the human GluR4B-encoding DNA in a specimen, such as brain tissue. This can be done using either the intact coding region, or a fragment thereof having radiolabelled e.g. $^{32}$P, nucleotides incorporated therein. To identify the human GluR4B-encoding DNA in a specimen, it is desirable to use either the full length cDNA coding therefor, or a fragment which is unique thereto. With reference to FIG. 1 and SEQ ID NO:1, such nucleotide fragments include these comprising at least about 17 nucleic acids, and otherwise corresponding in sequence to a region coding for the extracellular N-terminal or C-terminal region of the receptor, or representing a 5'-untranslated or 3'-untranslated region thereof. Such oligonucleotide sequences, and the intact gene itself, may also be used of course to clone human GluR4B-related human genes, particularly cDNA equivalents thereof, by standard hybridization techniques.

EXAMPLE 1

Isolation of DNA Coding for the Human GluR4B Receptor cDNA coding for the human GluR4B receptor was identified by probing human fetal brain cDNA that was obtained as an EcoRI-based lambda phage library (lambda ZAP) from Stratagene Cloning Systems (La Jolla, Calif., U.S.A.). The cDNA library was screened using two oligonucleotide probes capable of annealing to the rat GluR4 receptor sequence reported by Keinanen et al, supra. The specific sequences of the $^{32}$P-labelled probes are provided below:

(SEQ ID NO:3)
5'-ATGCATCGGAAGCTCCTTTCAATTTGGTACCT CATGTGGA-3'

(SEQ ID NO:4)
5'-AGTGTGGGAGAAAACGGCCGTGTGCTGACC CCTGACTGCC-3'

The fetal brain cDNA library was screened under the following hybridization conditions; 6×SSC, 25% formamide, 5% Dernhardt's solution, 0.5% SDS, 100 ug/ml denatured salmon sperm DNA, 42C. Filters were washed with 2×SSC containing 0.5% SDS at 25C for 5 minutes, followed by a 15 minute wash at 50C with 2×SSC containing 0.5% SDS. The final wash was with 1×SSC containing 0.5% SDS at 50C for 15 minutes. Filters were exposed to X-ray film (Kodak) overnight. Of $10^5$ clones screened, two cDNA inserts were identified, one about 2.4 kb, designated RKCSFG43, and another about 4.2 kb, designated RKC-SFG102. For sequencing, the '43 and '102 phages were plaque purified, then excised as phagemids according to the suppler's specifications, to generate insert-carrying Bluescript-SK variants of the phagemid vectors. Sequencing of the '43 clone across its entire sequence revealed a putative ATG initiation codon together with about 43 bases of 5'non-coding region and 2.4 kilobases of coding region. Sequencing across the '102 insert revealed significant overlap with the '43 insert, and also revealed a termination codon, as well as about 438 bases of 3' non-translated sequence.

To provide the entire coding region in an intact clone, the strategy shown in FIG. 2 was employed, to generate the phagemid pBS/humGluR4B which carries the human GluR4B-encoding DNA as a 4.0 kb EcoRi/Hindlll insert in a 3.0 kb Bluescript-SK phagemid background. The entire sequence of the EcoRi/Hindlll insert is provided in FIGS. 1A–1G.

This phagemid, pBS/humGluR4B, was deposited under the terms of the Budapest Treaty with the American Type Culture Collection in Rockville, Md. USA on Jul. 21, 1992, and has been assigned accession number ATCC 75279.

EXAMPLE 2

Construction of Genetically Engineered Cells Producing Human GluR4B Receptor

For transient expression in mammalian cells, cDNA coding for the human GluR4B receptor was incorporated into the mammalian expression vector pcDNA1, which is available commercially from invitrogen Corporation (San Diego, Calif., USA; catalogue number V490-20). This is a multifunctional 4.2 kb plasmid vector designed for cDNA expression in eukaryotic systems, and cDNA analysis in prokaryotes. Incorporated on the vector are the CMV promoter and enhancer, splice segment and polyadenylation signal, an SV40 and Polyoma virus origin of replication, and M13 origin to rescue single strand DNA for sequencing and mutagenesis, Sp6 and T7 RNA promoters for the production of sense and anti-sense RNA transcripts and a Col E1-like high copy plasmid origin. A polylinker is located appropriately downstream of the CMV promoter (and 3' of the T7 promoter).

Figure 3:
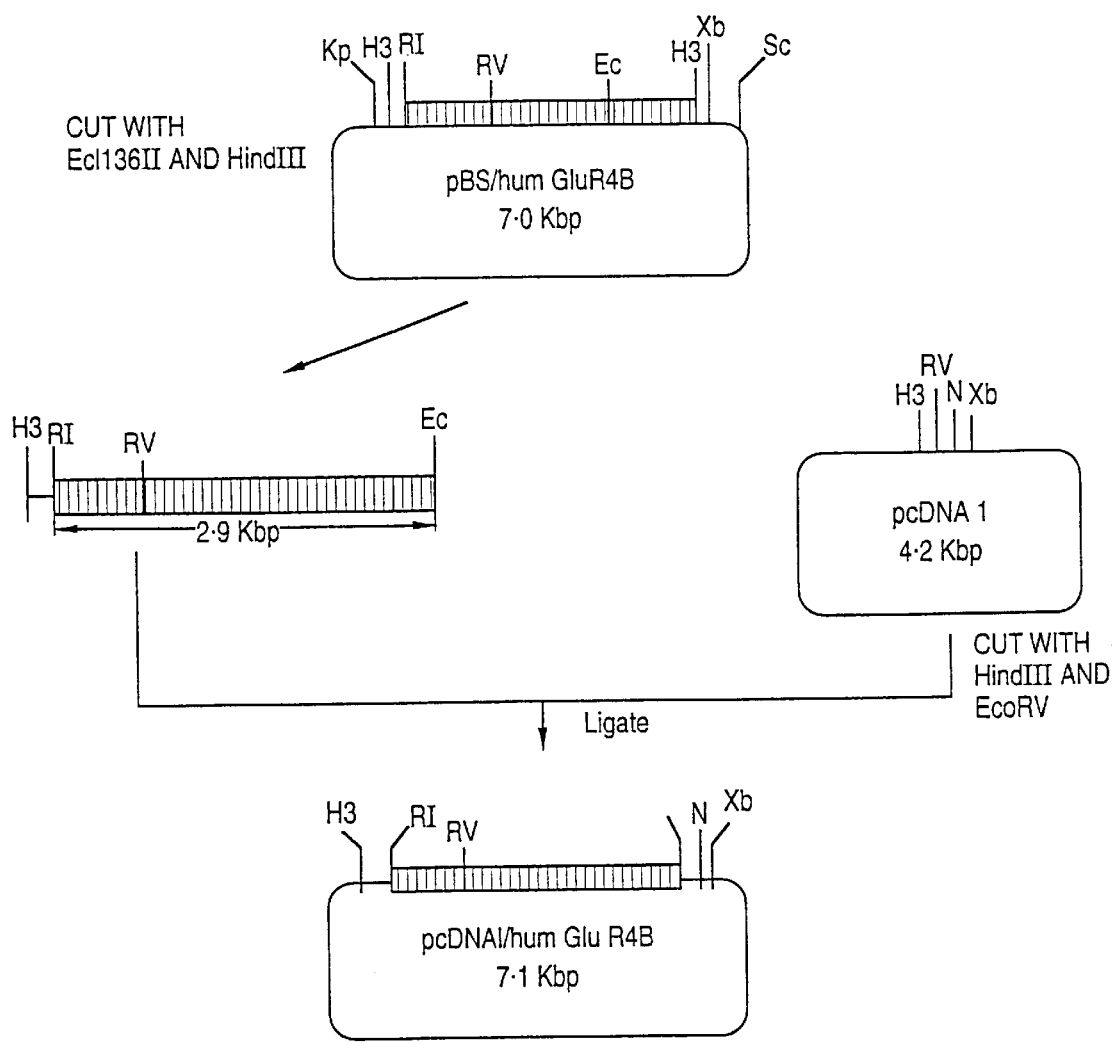
FIG. 3 depicts the strategy employed in generating recombinant DNA expression constructs incorporating the human GluR4B receptor-encoding DNA of FIGS. 1A–1G, where N is NotI, Sc is SacI, RI is EcoRI, RV is EcoRV, Kp is KpnI, H3 is HindIII, Ec is Eclo 136II and Xb is Xbe I.

The strategy depicted in FIG. 3 was employed to facilitate incorporation of the GluR4B receptor-encoding cDNA into an expression vector. The cDNA insert was first released from pBS/humGluR4B as a 2.9 kb HindIII/Ecl136II fragment, which was then incorporated at the Hindlll/EcoRV sites in the pcDNAI polylinker, Sequencing across the junctions was performed, to confirm proper insert orientation in pcDNAI. The resulting plasmid, designated pcDNAI/humGluR4B, was then introduced for transient expression into a selected mammalian cell host, In this case the monkey-derived, fibroblast like cells of the COS-1 lineage (available from the American Type Culture Collection, Rockville, Md. as ATCC CRL 1650).

For transient expression of the GluR4B-encoding DNA, COS-1 cells were transfected with approximately 8 ug DNA (as pcDNA1/humGluR2B) per $10^6$ COS cells, by DEAE-mediated DNA transfection and treated with chloroquine according to the procedures described by Maniatis et al, supra. Briefly, COS-1 cells were plated at a density of $5\times10^6$ cells/dish and then grown for 24 hours in FBS-supplemented DMEM/F12 medium. Medium was then removed and cells were washed in PBS and then in medium. There was then applied on the calls 10 ml of a transfection solution containing DEAE dextran (0.4 mg/ml), 100 uM chloroquine, 10% NuSerum, DNA (0.4 mg/ml) in DMEM/F12 medium. After incubation for 3 hours at 37C, cells were washed in PBS and medium as just described and then shocked for 1 minute with 10% DMSO in DMEM/F12 medium. Cells were allowed to grow for 2–3 days in 10% FBS-supplemented medium, and at the end of incubation dishes were placed on ice, washed with ice cold PBS and then removed by scraping. Cells were then harvested by centrifugation at 1000 rpm for 10 minutes and the cellular pellet was frozen in liquid nitrogen, for subsequent use in ligand binding assays. Northern blot analysis of a thawed aliquot of frozen cells confirmed expression of receptor-encoding cDNA in cells under storage.

In a like manner, stably transfected cell lines can also prepared using two different cell types as host: CHO K1 and CHO Pro5. To construct these cell lines, cDNA coding for human GluR4B is incorporated into the mammalian expression vector pRC/CMV (Invitrogen), which enables stable expression. Insertion at this site placed the cDNA under the expression control of the cytomegalovirus promoter and upstream of the polyadenylation site and terminator of the bovine growth hormone gene, and into a vector background comprising the neomycin resistance gene (driven by the SV40 early promoter) as selectable marker.

To introduce plasmids constructed as described above, the host CHO cells are first seeded at a density of $5\times10^5$ in 10% FBS-supplemented MEM medium. After growth for 24 hours, fresh medium are added to the plates and three hours later, the calls are transfected using the calcium phosphate-DNA co-precipitation procedure (Maniatis et al, supra). Briefly, 3 ug of DNA is mixed and incubated with buffered calcium solution for 10 minutes at room temperature. An equal volume of buffered phosphate solution is added and the suspension is incubated for 15 minutes at room temperature. Next, the incubated suspension is applied to the cells for 4 hours, removed and cells were shocked with medium containing 15% glycerol. Three minutes later, calls are washed with medium end incubated for 24 hours at normal growth conditions. Cells resistant to neomycin are selected in 10% FBS-supplemented alpha-MEM medium containing G418 (1 mg/ml). Individual colonies of G418-resistant cells are isolated about 2–3 weeks later, clonally selected and then propogated for assay purposes.

EXAMPLE 3

Ligand Binding Assays

Transfected cells in the frozen state were resuspended in ice-cold distilled water using a hand homogenizer, sonicated for 5 seconds, and then centrifuged for 20 minutes at 50,000 g. The supernatant was discarded and the membrane pellet stored frozen at −70C.

COS cell membrane pallets were suspended in ice cold 50 mM Tris-HCl (pH 7.55, 5C) and centrifuged again at 50,000 g for 10 minutes in order to remove endogenous glutamate that would compete for binding. Pellets were resuspended in ice cold 50 mM Tris-HCl (pH 7.55) buffer and the resultant membrane preparation was used as tissue source for binding experiments described below. Proteins were determined using the Pierce Reagent with B5A as standard.

Binding assays were then performed, using an amount of COS-derived membrane equivalent to from 25–100 ug as judged by protein determination and selected radiolabelled ligand. In particular, for AMPA-binding assays, incubation mixtures consisted of 25–100 ug tissue protein and D,L-alpha-[5-methyl-3H]amino-3-hydroxy-5-methylisoxazole-4-proplonic acid (3H-AMPA, 27.6 Ci/mmole, 10 nM final) with 0.1M KSCN and 2.5 mM $CaCl_2$ in the 1 ml final volume. Non-specific binding was determined in the presence of 1 mM L-glutamate. Samples were incubated on ice for 60 minutes in plastic minivials, and bound and free ligand were separated by centrifugation for 30 minutes at 50,000 g. Pellets were washed twice in 4 ml of the cold incubation buffer, then 5 ml of Beckman Ready-Protein Plus scintillation cocktail was added, for counting.

For kainate-binding assays, incubation mixtures consisted of 25–100 ug tissue protein and [vinylidene-3H] kainic acid (58 Cl/mmole, 5 nM final) in the cold incubation buffer, 1 ml final volume. Non-specific binding was determined in the presence of 1 mM L-glutamate. Samples were incubated as for the AMPA-binding assays, and bound and free ligand were separated by rapid filtration using a Brandel cell harvester and GF/B filters pre-soaked in ice-cold 0.3% polyethyleneimine. Filters were washed twice in 6 ml of the cold incubation buffer, then placed in scintillation vials with 5 ml of Beckman Ready-Protein Plus scintillation cocktail for counting.

Assays performed in this manner, using membrane preparations derived from the human GluR4B receptor-producing COS cells, revealed specific binding of about 92 fmole/mg protein, at 200 nM [3H]-AMPA (FIG. 4). Mock transfected cells exhibited no specific binding of any of the ligands tested. These results demonstrate clearly that the human GluR4B receptor is binding AMPA with specificity. This activity, coupled with the fact that there is little or no demonstrable binding of either kainate or NMDA, clearly assigns the human GluR4B receptor to be of the AMPA type of EAA receptor. Furthermore, this binding profile indicates that the receptor is binding in an authentic manner, and can therefore reliably predict the ligand binding "signature" of its non-recombinant counterpart from the human brain. These features make the recombinant receptor especially useful for selecting and characterizing ligand compounds which bind to the receptor, and/or for selecting and characterizing compounds which may act by displacing other ligands from the receptor. The isolation of the GluR4B receptor genes in substantially pure form, capable of being expressed as a single, homogeneous receptor species, therefore frees the ligand binding assay from the lack of precision introduced when complex, heterogeneous receptor preparations from human and other mammalian brains are used to attempt such characterizations.

We claim:

1. A membrane preparation derived from a host cell, said host cell having incorporated expressibly therein a heterologous polynucleotide that encodes human GluR4B receptor having the sequence of amino acids 1–881 of SEQ ID NO:2, wherein said receptor is expressed.

* * * * *